United States Patent
Lu et al.

(10) Patent No.: US 9,642,873 B2
(45) Date of Patent: May 9, 2017

(54) COMBINATIONS OF TGFβ AND COX-2 INHIBITORS AND METHODS FOR THEIR THERAPEUTIC APPLICATION

(75) Inventors: Patrick Y. Lu, Rockville, MD (US); Vera Simonenko, Germantown, MD (US); David Evans, North Potomac, MD (US); John J. Xu, Germantown, MD (US)

(73) Assignee: Sirnaomics, Inc., Gaithersburg, MD (US)

( * ) Notice: Subject to any disclaimer, the term of this patent is extended or adjusted under 35 U.S.C. 154(b) by 73 days.

(21) Appl. No.: 13/695,073

(22) PCT Filed: May 4, 2011

(86) PCT No.: PCT/US2011/035273
§ 371 (c)(1),
(2), (4) Date: May 2, 2013

(87) PCT Pub. No.: WO2011/140285
PCT Pub. Date: Nov. 10, 2011

(65) Prior Publication Data
US 2013/0225655 A1 Aug. 29, 2013

Related U.S. Application Data

(60) Provisional application No. 61/331,372, filed on May 4, 2010.

(51) Int. Cl.
| | | |
|---|---|---|
| C07H 21/04 | (2006.01) |
| C07H 21/02 | (2006.01) |
| A61K 48/00 | (2006.01) |
| A61K 31/713 | (2006.01) |
| C12N 15/113 | (2010.01) |
| A61K 45/06 | (2006.01) |

(52) U.S. Cl.
CPC ............ *A61K 31/713* (2013.01); *A61K 45/06* (2013.01); *C07H 21/02* (2013.01); *C12N 15/113* (2013.01); *C12N 15/1136* (2013.01); *C12N 15/1137* (2013.01); *C12Y 114/99001* (2013.01); *C12N 2310/14* (2013.01); *C12N 2320/11* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 7,070,807 B2 | 7/2006 | Mixson | |
| 7,163,695 B2 | 1/2007 | Mixson | |
| 7,772,201 B2 | 8/2010 | Mixson | |
| 8,541,568 B2 | 9/2013 | Yan et al. | |
| 8,735,567 B2 * | 5/2014 | Lu et al. | ............ 536/24.5 |
| 9,012,622 B2 | 4/2015 | Lu et al. | |
| 2005/0176024 A1 | 8/2005 | McSwiggen et al. | |
| 2006/0121514 A1 | 6/2006 | Young et al. | |
| 2006/0134787 A1 | 6/2006 | Zamore et al. | |
| 2006/0265765 A1 | 11/2006 | Agatsuma et al. | |
| 2007/0003519 A1 | 1/2007 | Lu et al. | |
| 2008/0015161 A1 | 1/2008 | Vornlocker et al. | |
| 2008/0241198 A1 | 10/2008 | Liu et al. | |
| 2010/0319074 A1 * | 12/2010 | Lu et al. | ............ 800/3 |

FOREIGN PATENT DOCUMENTS

| | | | | |
|---|---|---|---|---|
| WO | WO 0147496 A1 | 7/2001 | | |
| WO | WO 03040399 A2 | 5/2003 | | |
| WO | WO 03070918 A2 | 8/2003 | | |
| WO | WO 03090719 A1 | 11/2003 | | |
| WO | WO 2005076999 A2 | 8/2005 | | |
| WO | WO 2006060182 A2 | 6/2006 | | |
| WO | WO2007079224 | * | 7/2007 | ............ C12N 15/11 |
| WO | WO2009061417 | * | 5/2009 | ............ A61K 31/70 |

OTHER PUBLICATIONS

International Search Report of the International Searching Authority on International App. No. PCT/US2011/035273 (WO 2011/140285) of Sirnaomics, Inc., Jan. 27, 2012.

Cheema, Sangeeta, et al., "Regulation and Guidance of Cell Behavior for Tissue Regeneration Via the Sima Mechanism", Wound Repair and Regeneration, vol. 15, No. 3, 2007, pp. 286-295.

Choi, Byung-Min, et al., "Control of Scarring in Adult Wounds Using Antisense Transforming Growth Factor-Beta1 Oligodeoxynucleotides", Immunology and Cell Biology, vol. 74, 1996, pp. 144-150.

De Wolf, Holger, et al., "Effect of Cationic Carriers on the Pharmacokinetics and Tumor Localization of Nucleic Acids after Intravenous Administration," International Journal of Pharmaceutics, 331, 2007, pp. 167-175.

Leng, Qixin, et al., "Highly Branched HK Peptides Are Effective Carriers of siRNA," The Journal of Gene Medicine, 2005, 7, pp. 977-986.

Pickering, Lulu, "Progress in RNA-based therapeutics," Spectrum Drug Discovery and Design, Decisio Resources, Inc., Waltham, Massachusetts, Aug. 4, 2005, pp. 6-1 to 6-20.

Wilgus, Traci, et al, "Reduction of Scar Formation in Full-Thickness Wounds With Topical Celecoxib Treatment", Wound Repair and Regeneration, Mosby-Year Book, St. Louis, Mo, US, vol. 11, 2003, pp. 25-34.

Reissue U.S. Appl. No. 15/166,223, filed May 26, 2016 for "Multi-Targeted RNAi Therapeutics for Scarless Wound Healing of Skin," including Preliminary Amendment filed May 27, 2016.

* cited by examiner

*Primary Examiner* — Jennifer McDonald
(74) *Attorney, Agent, or Firm* — Geoffrey M. Karny

(57) ABSTRACT

The present invention provides compositions and methods for using combinations of TGFβ1 and Cox-2 inhibitors and TGFβ1 and Hoxb13 inhibitors for the treatment of various medical conditions, including skin scaring due to trauma wounds and surgery, corneal and retina scaring due to injury and surgery, internal organ scaring due to injury and surgery, heart tissue scaring due to heart attack and surgery, and lung, liver, and kidney fibrosis due to inflammation and injury. One example is to use siRNA inhibitors to silence TGFβ1 and Cox-2 at the same time, resulting in significant less scar formation.

37 Claims, 25 Drawing Sheets

Screening Potent siRNA Inhibitors

PC-3 cell, prostate carcinoma cell line with high expressions of TGFβ1, Cox-2 and Hoxb13.

Total RNA was isolated after siRNA transfection and followed with Q-RT-PCR using MyiQ thermocycler from Bio-Rad.

Selecting the most potent siRNA from eight siRNA duplexes targeting each gene, with homology to both human and mouse sequences, using Q-RT-PCR following cell culture transfection experiments

COMBINATIONS OF TGFβ AND COX-2 INHIBITORS AND METHODS FOR THEIR THERAPEUTIC APPLICATION

CROSS-REFERENCE TO RELATED PATENT APPLICATIONS

This application is a U.S. national phase application of, and claims the benefit of and priority to, International Patent Application No. PCT/US2011/035273, filed May 4, 2011, which claims the benefit of and priority to U.S. Provisional Patent Application No. 61/331,372, filed May 4, 2010. The disclosures of these applications are expressly incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Apr. 29, 2013, is named SIR_008_P001_US_SL.txt and is 20,068 bytes in size.

FIELD OF THE INVENTION

The present invention provides compositions of TGFβ1 and Cox-2 inhibitors and methods for using the combinations for treatment of various human conditions, including, but not limited to, skin scarring due to trauma wounds and surgery, corneal and retina scarring due to injury and surgery, internal organ scarring due to injury and surgery, heart tissue scarring due to heart attack and surgery, and lung, liver, and kidney fibrosis due to inflammation and injury.

BACKGROUND

TGFβ Antibody Partially Reduced the Amount of Scarring

Evidence demonstrates that wound healing is regulated by a group of cytokines, growth factors and their receptors (5-7). They influence cell migration, growth and proliferation in a complex, orchestrated manner and are involved in neutrophil and macrophage infiltration, angiogenesis, fibroplasia, matrix deposition, scarring and reepithelialization. Besides platelets and macrophages, fibroblasts are the major cellular source of cytokines or growth factors during wound healing. The scarless wound healing in fetal skin at early gestation is a result of the unique cytokine or growth factor profile.

Of these, transforming growth factor-beta (TGFβ3) has been most widely studied as it is implicated in the transition between scarless healing and repair with scar formation. Called growth factors for historical reasons, their main function is to control cell proliferation and differentiation and to stimulate the synthesis of extracellular matrix such as collagen. TGFβ has been found by immunohistochemistry in unwounded fetal skin, and high levels of TGFβ are expressed at gestational ages associated with scarless repair. Exogenous application of TGFβ to normally scarless fetal wounds resulted in scar formation and an adult-like inflammatory response was observed. The profibrotic nature of TGFβ was confirmed in wounds of adult rats as a neutralizing TGFβ antibody partially reduced the amount of scarring. TGFβ stimulates collagen I production, which is the predominant collagen type in adult skin. On the other hand, TGFβ neutralizing antibodies do not entirely prevent scarring in the adult skin, and recent studies question the efficacy of TGFβ as a dominant scar-forming factor (8-15).

Studies have also found that decreased and rapidly cleared TGFβ1 and TGFβ2 expression accompanied by increased and prolonged TGFβ3 levels in wounded E16 animals correlated with organized collagen deposition. In contrast, increased and prolonged TGFβ1 and TGFβ2 expression accompanied by decreased and delayed TGFβ3 expression in wounded E19 animals correlated with disorganized collagen architecture. This means that increased TGFβ1, TGFβ2, and decreased TGFβ3 expression is responsible for the late gestation fetal scar formation.

COX-2 Inhibitor Reduces Scar Tissue Formation and Enhances Tensile Strength

While the interleukins IL-6, IL-8, and IL-10 have been studied in fetal wound repair, COX-2 has also received much attention recently as it is involved in diseases associated with dysregulated inflammatory conditions, such as rheumatoid and osteoarthritis, cardiovascular disease, and the carcinogenesis process (16-20). COX-2 undergoes immediate-early up-regulation in response to an inflammatory stimulus (20, 21), such as a wound. It functions by producing prostaglandins that control many aspects of the resulting inflammation, including the induction of vascular permeability and the infiltration and activation of inflammatory cells (22). Interest in the role of the COX-2 pathway and other aspects of inflammation in the adult wound repair process is increasing (35) as these early events have been shown to regulate the outcome of repair. Based on the involvement of COX-2 in inflammation and the recent demonstration that it contributes to several aspects of adult wound repair (23-25), the role of COX-2 in the fetal wound healing process has been examined. These studies demonstrate differential expression of the COX-2 enzyme in early and late gestation fetal wounds.

Furthermore, $PGE_2$, a COX-2 product shown to mediate many processes in the skin, caused a delay in healing and the production of a scar when introduced into early fetal wounds. The involvement of the COX-2 pathway in scar formation is further highlighted by the fact that increasing $PGE_2$ levels in scarless wounds results in the conversion of a scarless healing process into one of repair with the generation of a scar. The introduction of $PGE_2$ induced inflammation in fetal wounds (26), although their effect on collagen deposition or fibrosis was not examined. Whether $PGE_2$ displays immunosuppressive or anti-inflammatory properties or instead acts as a pro-inflammatory molecule most likely results from differences in the expression or activity of the receptors for $PGE_2$. There are several plausible mechanisms by which $PGE_2$ could be inducing scar formation in fetal wounds. $PGE_2$ could be enhancing acute inflammation, already known to interfere with scarless healing, thereby indirectly promoting scar formation through the recruitment and activation of inflammatory cells. $PGE_2$ treatment could be both delaying healing and promoting scar tissue deposition through increases in the pro-fibrotic TGFβ (27). Disruption of the TGFβ signaling pathway in smad3-deficient mice has been shown to speed the rate of healing, and extensive data demonstrates restricted TGFβ3 levels are crucial to scarless healing. Lastly, there are data demonstrating increased fibroblast proliferation in response to $PGE_2$ suggests that $PGE_2$ could be directly stimulating fibroblasts to proliferate, amplifying collagen production and scarring. This idea is also supported by previous studies demonstrating an increase in collagen deposition and proliferation by fibroblasts following exposure to $PGE_2$. The substantial data suggested the low levels of COX-2 expression and $PGE_2$ may be necessary for the scarless repair of fetal skin. The fact that $PGE_2$ induces scar formation in fetal skin further supports a role for the COX-2 pathway in scar formation.

Using a COX-2 inhibitor celecoxib to treat incisional wounds, the role of COX-2 in the wound healing process was examined with significant inhibition of several parameters of inflammation in the wound site (28). This decrease in the early inflammatory phase of wound healing had an effect on later events in the wound healing process, namely a reduction in scar tissue formation, without disrupting reepithelialization or decreasing tensile strength.

Multi-Targeted siRNA Compositions

RNA interference (RNAi) is a sequence-specific RNA degradation process that provides a relatively easy and direct way to knockdown, or silence, theoretically any gene (33, 34). In naturally occurring RNA interference, a double stranded RNA is cleaved by an RNase III/helicase protein, Dicer, into small interfering RNA (siRNA) molecules, a dsRNA of 19-23 nucleotides (nt) with 2-nt overhangs at the 3' ends. These siRNAs are incorporated into a multicomponent-ribonuclease called RNA-induced-silencing-complex (RISC). One strand of siRNA remains associated with RISC, and guides the complex towards a cognate RNA that has sequence complementary to the guider ss-siRNA in RISC. This siRNA-directed endonuclease digests the RNA, thereby inactivating it. Studies have revealed that the use of chemically synthesized 21-25-nt siRNAs exhibit RNAi effects in mammalian cells, and the thermodynamic stability of siRNA hybridization (at terminals or in the middle) plays a central role in determining the molecule's function (33, 36, 37).

Importantly, it is presently not possible to predict with high degree of confidence which of many possible candidate siRNA sequences potentially targeting an mRNA sequence of a disease gene will, in fact, exhibit effective RNAi activity. Instead, individually specific candidate siRNA polynucleotide or oligonucleotide sequences must be generated and tested in mammalian cell culture to determine whether the intended interference with expression of a targeted gene has occurred. The unique advantage of siRNA makes it possible to be combined with multiple siRNA duplexes to target multiple disease causing genes in the same treatment, since all siRNA duplexes are chemically homogenous with same source of origin and same manufacturing process (33, 36-40).

There is a pressing need to provide potent siRNA duplexes targeting the pro-inflammatory factor TGFβ1, the inflammation promoter COX-2, and the differentiation regulator HoxB1 for scarless wound healing of skin. There further is a need to formulate such siRNA duplexes into multi-targeted siRNA compositions. There further remains a need to provide a therapeutic approach to improve the healing results of patients suffering wounds caused by injury, surgery, and many diseases.

Histidine-Lysine Polymer (HKP) Nanoparticle for SiRNA Delivery In Vivo

Histidine-Lysine Polymer (HKP), a cationic branched polymer, has been used for plasmid DNA and siRNA delivery in vivo. Recently, we have used HKP for siRNA delivery in various tissue types, including tumor, ocular, brain, lung and joint. A pair of the HK polymer species, H3K4b and PT73, has a Lysine backbone with four branches containing multiple repeats of Histidine, Lysine or Asparagine. When this HKP aqueous solution was mixed with siRNA at a N/P ratio of 4:1 by mass, the nanoparticles (average size of 100-200 nm in diameter) were self-assembled.

DESCRIPTION OF THE INVENTION

Figure 1:
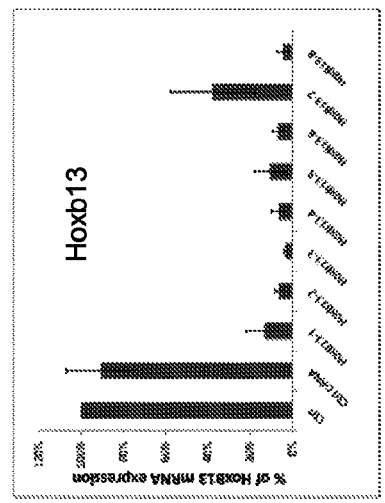
FIG. 1. In Vitro Screening of Potent siRNA Sequences. Eight siRNA sequences were designed using our proprietary algorithm against each gene target, TGFβ1, Cox-2 and Hoxb13. PC-3 cell (human prostate carcinoma cell line) was transfected with the siRNA sequences followed by total RNA isolation and Quantitative RT-PCR using MyiQ thermocycler. The most potent siRNA against each gene were selected based on the gene silencing effects.
Figure 1:
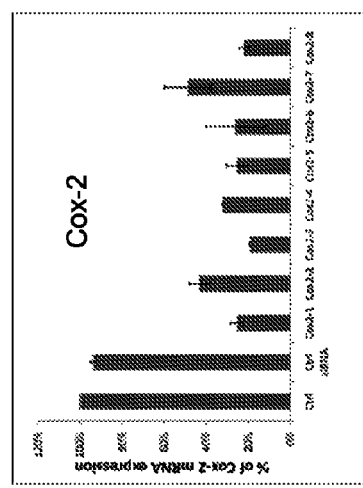
Figure 1:
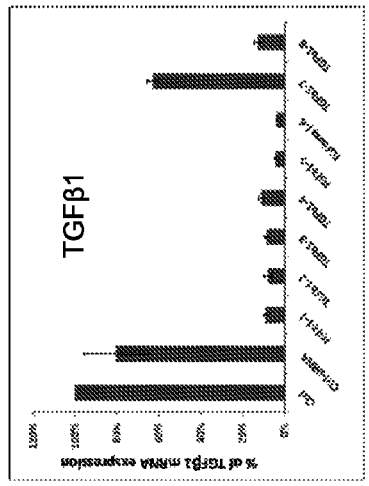

The present invention relates to compositions of TGFβ1 and Cox-2 inhibitors and to methods for using the combinations for treatment of various medical conditions. As used herein, the term "inhibitor" means any chemical substance, generally a molecule, that inhibits the activity of the targeted gene, RNA, or protein, as the case may be, in vitro or in vivo. For example, the inhibitors can be small molecules, peptides, monoclonal antibodies, aptamers, antisense molecules, or siRNA molecules.

In one embodiment, the invention provides a composition comprising an inhibitor of TGFβ1 and an inhibitor of Cox-2. In another embodiment, the composition further comprises an inhibitor of Hoxb13. In a further embodiment, the composition comprises an inhibitor of TGFβ1 and an inhibitor of Hoxb13. In still another embodiment, these compositions include a pharmaceutically acceptable carrier.

In one embodiment, the invention provides a composition comprising an siRNA molecule that targets and binds to an mRNA molecule that codes for TGFβ1 protein in a mammalian cell and an siRNA molecule that targets and binds to an mRNA molecule that codes for Cox-2 protein in a mammalian cell. As shown in the Examples, combination of siRNA inhibitors targeting both TGFβ1 and Cox-2 genes demonstrated a unique therapeutic benefit superior to the single inhibitors or combinations other than these two. In one aspect of this embodiment, the composition further includes an siRNA molecule that targets and binds to an mRNA molecule that codes for Hoxb13 protein in a mammalian cell. In another aspect of this embodiment, the composition comprises an siRNA molecule that targets and binds to an mRNA molecule that codes for TGFβ1 protein in a mammalian cell and an siRNA molecule that targets and binds to an mRNA molecule that codes for Hoxb13 protein in a mammalian cell. In a further embodiment, the siRNA molecules are selected from the ones identified in Table 1. An example is the pair designated hmTF-25-2 and hmCX-25-1 in the table. The siRNA molecules can produce additive or synergistic effects in the cells, depending on the compositions and structures of the particular molecules.

As used herein, an "siRNA molecule" is a duplex oligonucleotide, that is a short, double-stranded polynucleotide, that interferes with the expression of a gene in a cell that produces RNA, after the molecule is introduced into the cell. For example, it targets and binds to a complementary nucleotide sequence in a single stranded (ss) target RNA molecule, such as an mRNA or a micro RNA (miRNA). The target RNA is then degraded by the cell. Such molecules are constructed by techniques known to those skilled in the art. Such techniques are described in U.S. Pat. Nos. 5,898,031, 6,107,094, 6,506,559, 7,056,704 and in European Pat. Nos. 1214945 and 1230375, which are incorporated herein by reference in their entireties.

In one embodiment, the molecule is an oligonucleotide with a length of about 19 to about 35 base pairs. In one aspect of this embodiment, the molecule is an oligonucleotide with a length of about 19 to about 27 base pairs. In another aspect, the molecule is an oligonucleotide with a length of about 21 to about 25 base pairs. In all of these aspects, the molecule may have blunt ends at both ends, or sticky ends at both ends, or a blunt end at one end and a sticky end at the other.

The siRNA molecule can be made of naturally occurring ribonucleotides, i.e., those found in living cells, or one or more of its nucleotides can be chemically modified by techniques known in the art. In addition to being modified at the level of one or more of its individual nucleotides, the backbone of the oligonucleotide can be modified. Additional modifications include the use of small molecules (e.g. sugar molecules), amino acid molecules, peptides, cholesterol, and other large molecules for conjugation onto the siRNA molecule.

The invention includes a method for identifying the desired siRNA molecules comprising the steps of: (a) creating a collection of siRNA molecules designed to target a complementary nucleotide sequence in the target mRNA molecules, wherein the targeting strands of the siRNA molecules comprise various sequences of nucleotides; (b) selecting the siRNA molecules that show the highest desired effect against the target mRNA molecules in vitro; (c) evaluating the selected siRNA molecules in an animal wound model; and (d) selecting the siRNA molecules that show the greatest efficacy in the model. In one aspect of this embodiment, the animal wound model is a back skin excisional wound model in a Balb/c mouse or a back excisional wound model in a pig. In another aspect, the animal wound model is a lip excisional wound model in a Hoxb13 knockout mouse or a back excisional wound model in a Hoxb13 knockout mouse. In another aspect, the animal wound model is a skin burn wound model in a pig. In a further aspect, the animal wound model is a back skin excisional wound model in a transgenic diabetic (db+/db+) mouse. Preferably, the siRNA molecules are evaluated in at least two of the animal models. In one embodiment, the method further includes the steps of adding a pharmaceutically acceptable carrier to each of the siRNA molecules selected by step (b) to form pharmaceutical compositions and evaluating each of the pharmaceutical compositions in the animal wound model or models.

In an alternative embodiment, the siRNA molecules are examined in an in vitro organ culture assay for their silencing activity and therapeutic efficacy.

In one embodiment, the siRNA sequences are prepared in such way that each one can target and inhibit the same gene from, at least, both human and mouse, or human and non-human primate. In one aspect, the siRNA molecules bind to both a human mRNA molecule and a homologous mouse mRNA molecule. That is, the human and mouse mRNA molecules encode proteins that are substantially the same in structure or function. Therefore, the efficacy and toxicity reactions observed in the mouse disease models provide a good understanding about what is going to happen in humans. More importantly, the siRNA molecules tested in the mouse model are good candidates for human pharmaceutical agents. The human/mouse homology design of an siRNA drug agent can eliminate the toxicity and adverse effect of those species specificities observed in monoclonal antibody drugs.

In one embodiment, the invention provides a composition comprising two or more different siRNA molecules that bind to an mRNA that codes for TGFβ1 protein in a mammalian cell and two or more different siRNA molecules that bind to an mRNA that codes for Cox-2 protein in a mammalian cell. In one aspect, these compositions further include two or more different siRNA molecules that bind to an mRNA that codes for Hoxb13 protein in a mammalian cell. In another embodiment, the composition comprises two or more different siRNA molecules that bind to an mRNA that codes for TGFβ1 protein in a mammalian cell and two or more different siRNA molecules that bind to an mRNA that codes for Hoxb13 protein in a mammalian cell. In still another embodiment, the compositions comprise three different siRNA molecules that bind to each of the target mRNAs. In all of these embodiments and aspects, the molecules may bind to different nucleotide sequences within the target mRNA. In all of these embodiments and aspects, the siRNA molecules can produce additive or synergistic effects in the cells, depending on the compositions and structures of the particular molecules. In certain applications of these embodiments, the siRNA molecules are selected from the ones identified in Table 1.

In one embodiment, the siRNA molecules are combined with a pharmaceutically acceptable carrier to provide pharmaceutical compositions for administering to a subject. The subject may be any mammal. In one aspect, the mammal is a laboratory animal, which includes dogs, cats, pigs, non-human primates, and rodents, such as mice, rats, and guinea pigs. In another aspect, the mammal is a human.

In various embodiments of the composition, the carrier comprises one or more components selected from the group consisting of a saline solution, a sugar solution, a polymer, a peptide, a lipid, a cream, a gel, a micellar material, a silica nanoparticle, a plasmid, and a viral vector. Other carriers include one or more of the following: a polycationic binding agent, cationic lipid, cationic micelle, cationic polypeptide, hydrophilic polymer grafted polymer, non-natural cationic polymer, cationic polyacetal, hydrophilic polymer grafted polyacetal, ligand functionalized cationic polymer, and ligand functionalized-hydrophilic polymer grafted polymer, biodegradable polyesters, such as poly(lactic acid) (PLA), poly(glycolic acid) (PGA), and poly(lactic-co-glycolic acid) (PLGA), and polyamidoamine (PAMAM) dendrimers. In further embodiments of the composition, the carrier is a histidine-lysine copolymer that forms a nanoparticle containing an siRNA molecule, wherein the nanoparticle has a size of 100-400 nm in diameter. In another embodiment, the carrier comprises a 1, 1.5, 2, 3, or 10 percent concentration of methylcellulose aqueous solution. Preferably, the carrier is suitable for topical administration. More than one type of carrier can be used.

siRNA-mediated therapy not only depends on identification of the targets and the sequences of active siRNA molecules, but also on efficient in vivo delivery to the target tissues and into the cytoplasm (41-43). Preferably, the routes of delivery of siRNA formulations for treatment of skin wound healing are local and topical with appropriate clinically validated carriers. In addition to using imiquimod 5% cream as a carrier for topical application, three polymer-based carriers, including histidine-lysine polymers (HKP) (44), pegylated PEI (45), and PAMAM dendrimer (46) are useful carriers.

The compositions of the invention are useful for treating a wound in a mammal. A therapeutically effective amount of the composition (or compositions) is (are) administered the to the wound or to the mammal. The doseages, methods, and times of administration are readily determinable by a person skilled in the art, given the teachings contained herein. The wound can be in the skin (e.g., epidermis, dermis, and full thickness), eye (e.g., cornea and retina), muscle, arterial walls, venous walls, or internal an organ. The wound may be characterized at least in part by inflammation and neovascularization. It may be caused by trauma, an allergy, diabetic disease, inflammation, or a tumor. Trauma includes excision, incision, surgery, cuts, burns, and acute injury. In one aspect, the wound is an ulcer, such as a diabetic foot ulcer, pressure ulcer, arterial ulcer, psoriases ulcer, and venous ulcer. In another aspect, the wound is the result of corneal replacement surgery or retina surgery. Preferably, the treatment results in minimized scar formation compared to the scar that would be formed without treatment.

The compositions are also useful for treating tissue fibrosis caused by scaring after chronic inflammation of the tissue. Such tissues include the liver, lung, kidney, and heart. A therapeutically effective amount of the compositions are administered to the mammal or the wound.

Since the invention is broadly directed to combinations of TGFβ and Cox-2 inhibitors, it is not limited to any particular type of inhibitor. The siRNA combinations described herein can also be used with combinations of the other types of chemical substances described above, such as small molecules, peptides, monoclonal antibodies, aptamers, and antisense molecules.

The following examples illustrate certain aspects of the invention and should not be construed as limiting the scope thereof.

EXAMPLES

Materials and Methods

Cell Culture

Human PC3 cells (prostate adenocarcinoma, ATCC-formulated F-12K Medium), mouse C166 (yolk sac, endothelial, ATCC-formulated Dulbecco's Modified Eagle's Medium) were purchased from the American Type Culture Collection. To make the complete growth medium fetal bovine serum was added to a final concentration of 10%. Cells were incubated at 37° C. in 5% $CO_2$.

siRNA Design

Eight 25mer blunt-ended siRNA duplexes targeting TGFβ1, Cox-2 and HoxB13 mRNA sequences were designed (Table 1). Each sequence is homologous for corresponding genes between human, mouse and pig. Eight siRNA oligos for each gene were tested in human PC3 cells and mouse C166 cells. siRNA oligonucleotides for cell transfection were synthesized by Qiagen, Valencia, Calif., oligonucleotides for in vivo topical application were purchased from Dharmacon.

siRNA Mediated Gene Silencing In Vitro $2.5 \times 10^5$ cells were seeded on the wells of 6-well plates on the day before transfection in 2 ml ATCC-formulated appropriate medium with 10% fetal bovine serum (37° C., air 100%). On the next day cells were transfected with siRNA oligos using Lipofectamin2000 (Invitrogen). Oligomer-Lipofectamine 2000 complexes were prepared according to the manufacturer's recommendation. The siRNA for each sample was diluted in 250 μl Opti-MEM I reduced serum free medium, Lipofectamine 2000 was diluted with Optimem I Reduced Serum Medium with a ratio of 1:50, and after 5 min incubation diluted oligomers were combined with 250 μl of diluted Lipofectamine 2000. After 20 min incubation at RT the mixtures were added drop-wise to each well. After 6 hours the medium was changed. Cells were incubated for 48 hours at 37° C. and then target mRNA level was analyzed. Total RNA was isolated from the cells with RNAqueous-4PCR kit (Ambion). Gene expression in transfected cells was analyzed with semi-quantitative reverse transcriptase-PCR and real-time PCR.

Semi-Quantitative Reverse Transcriptase-Polymerase Chain Reaction

Total cellular RNA was reverse transcribed using the GeneAmp Gold RNA PCR Reagent Kit accordingly to the manufacture's protocol (Applied Biosystems) using random hexamers. The primers sequences for human/mouse TGFβ1 RT-PCR were forward 5'-CTACTGTGTGCTGAGCAC-CTT-3' (SEQ ID NO: 1) and reverse 5'-CGCTGCTCGGC-CACTCTGGCT-3' (SEQ ID NO: 2), for human/mouse Cox-2 forward 5'-GGAAGCCTTCTCCAACCTCT-3' (SEQ ID NO: 3) and reverse 5'-GGATACACCTCTCCACCAAT-3' (SEQ ID NO: 4), for human/mouse HoxB13 forward 5'-CTCCAGCTCCTGTGCCTTAT-3' (SEQ ID NO: 5) and reverse 5'-CGCTGCTCGGCCACTCTGGCT-3' (SEQ ID NO: 2).

The cycling program was as follows: 94° C. 20s, 57° C.° 20s, 72° C. 30s x28 cycles. The RT-PCR products were 488bp for TGFβ1, 371 by for Cox-2 and 205bp for HoxB13. After separation of PCR products in 1.2% agarose gels and visualization with ethidium bromide, images were captured and bands were quantified using a FluorChem 8900 Multi-image light cabinet and image analysis software (Alpha Innotech). To normalize mRNA levels between different samples for an exact comparison of mRNA transcription levels a housekeeping gene Rig/S15 RNA was amplified with commercially available primers set for human and murine S15 RNA (Ambion, Austin, Tex.). Data are presented as a percentage of the gene expression in the non-treated control wound.

Real-Time PCR Analyses of Gene Expression in Transfected Cells and Wounded Skin Tissue Total RNA from harvested wound tissue was isolated using the RNeasy fibrous tissue mini Kit (Qiagen, Valencia, Ca). cDNAs were synthesized by iScript reverse transcription (Bio-Rad, Hercules, Ca) according to the manufacturer's instructions and then were diluted 6-fold in $H_2O$ and employed in semiquantitative real-time PCRs that used the SYBR Green system supplemented with 12.5 μl of diluted cDNA. Primers concentration was 600nM. PCRs were performed on Bio-Rad MyiQ Thermal Cycler and levels of genes expression were normalized to the housekeeping gene β-actin. Following primers were used; for mouse TGFβ1 5'-GTGCGGCAGCTGTACATTGACTTT-3' (SEQ ID NO: 6) and 5'-TGTGTTGGTTGTAGAGGGCAAGGA-3' (SEQ ID NO: 7), for mouse Cox-2 5'-ACTGGGCCATGGAGTG-GACTTAAA-3' (SEQ ID NO: 8) and 5'-AACTGCAGGT-TCTCAGGGATGTGA-3 (SEQ ID NO: 9), for mouse HoxB13 5'-ATGGCCAGTTACCTGGATGTGTCT-3' (SEQ ID NO: 10) and 5'-AGAATGGACCTGGTGGGTTCTGTT-3' (SEQ ID NO: 11), for mouse β-actin 5'-TGGTACCAC-CATGTACCCAGGCAT-3' (SEQ ID NO: 12) and 5'-ACTC-CTGCTTGCTGATCCACATCT-3' (SEQ ID NO: 13), for human TGFβ1 5'-GAGCCTGAGGCCGACTACTA-3' (SEQ ID NO: 14) and reverse 5'-CGGAGCTCTGATGTGT-TGAA-3' (SEQ ID NO: 15), for human Cox-2 5'-ATTC-CCTTCCTTCGAAATGC-3' (SEQ ID NO: 16) and 5'-GGGGATCAGGGATGAACTTT-3' (SEQ ID NO: 17), for pig TGFβ1 5' -TGTCACCGGAGTTGTGCGGC-3' (SEQ ID NO: 18) and 5'-GGGAGCTGTGCAGGTGCTGG-3' (SEQ ID NO: 19), for pig Cox-2 5'-ATCAGAAGCGAG-GACCAGCTTTCA-3' (SEQ ID NO: 20) and 5'-ACTT-GAGTGTCTTTGGCTGTCGGA-3' (SEQ ID NO: 21), for pig β-actin 5'-CACGCCATCCTGCGTCGGA-3' (SEQ ID NO: 22) and 5'-AGCACCGTGTGGCGTAGAG-3' (SEQ ID NO: 23).

Animals

Wounds Generation and Treatment

Mouse Model

Six to eight week old Balb/c mice (Taconic, N.Y.) were used for establishing a skin excision wound model. Excisional full-thickness skin wounds were made aseptically on the dorsal skin by picking up fold skin at the midline and punching through two layers of skin with sterile-disposable biopsy punch with a diameter of 5 mm (ACE Surgical Supply). Two wounds with a diameter of 5 mm were made at the same time, one wound on each side of midline. Four wounds were made on the same animal. Five mice per group were wounded and treated immediately by topical application of 50 μl/wound 1.5% Methylcellulose gel containing siRNA-HK-polymers formulation or siRNA alone or PBS. Treatment sustained for five consecutive days after wounding. Wounded tissue samples for RT-PCR analysis were harvested on the day 6 after wounding. The whole wounds were dissected and submerge in RNA-later solution (Ambion). For histological studies wound tissue was harvested on day 21 post-wounding, fixed in 4% paraformyldegide, processed by dehydration in alcohol and then embedded in paraffin wax. The mouse model experiments were approved by IACUC of Advanced Medical Research Institute, Rockville, Md., for excisional wound model.

Porcine Model

The pig models were approved by IACUC of Suchou University Central Facility of Experimental Animals including excisional wound modeling, burn wound modeling, tissue sampling.

Full Thickness Skin Excisional Wound

1. An ordinary domestic female piglet (Taihuzhu) of 15 kg in weight was anaesthetized with pentobarbital sodium at 40 mg/kg through ear vein injection. And respirator was applied for breathing assistance.

2. The piglet was put on the operation desk in a supine position, and hair was shaved off the back after sanitization with iodophor solution (1% w/v).

3. A full thickness skin wound was produced along the marked lines with an electric scalpel.

4. Experimental agents (formulated in HKP polymer and methylcellulose) were then applied daily to the wounds according to the experimental design for a total of 9 days.

5. Afterwards pictures were taken twice weekly to track changes. Biopsy samples were taken for pathology and IHC studies 30-40 days after the initial wounding.

Full Thickness Skin Burn Wound 1. and 2. Same as above.

3. A machine was used to create homogeneous skin burn wounds (the model is YLS-5Q Skin Burning Device). The settings are 1.5 kg for pressure, 90° C. for temperature, and for 30 seconds. All wounds are 2 $cm^2$ in size.

4. Eschars were shaved within 0.5-1.0 hour after the burning for one group of wounds, and after 72 hours for another group.

5. The rest was same as above.

Preparation of siRNA/HK Polymer Nanoplexes/Methylcellulose Solutions

Optimized histidine-lysine polymers (HKP) that have been applied for siRNA deliveries has a Lysine backbone with four branches containing multiple repeats of Histidine, Lysine or Asparagine. Optimal branched histidine-lysine polymer, HKP, was synthesized on a Ranin Voyager synthesizer (PTI, Tucson, Ariz.). The structure for HKP was (R)K(R)-K(R)-(R)K(X), where R=KHHHKHHHKHHHKHHHK, X=C(O)NH2, K=lysine, H=histidine. The HKP was dissolved in aqueous solution and then mixed with siRNA aqueous solution at a ratio of 4:1 by mass, forming nanoparticles of average size of 150-200 nm in diameter. The HKP-siRNA aqueous solution was semi-transparent without noticeable aggregation of precipitate, and can be stored at 4° C. for at least three months.

Based on results of experiments on in vitro gene expression down regulation, following potent 25 mer siRNA duplexes were selected for nanoplexes preparation: hmTGF-1: sense, 5'-CCCAAGGGCUACCAUGCCAACUUCU-3' (SEQ ID NO: 24), antisense, 5'-AGAAGUUGGCAUGGUAGCCCUUGGG-3' (SEQ ID NO: 25); hmCox-2: sense, 5'-GGUCUGGUGCCUGGUCUGAUGAUGU-3' (SEQ ID NO: 26), antisense, 5'-ACAUCAUCAGACCAGGCACCAGACC-3' (SEQ ID NO: 27); hmHoxB13: sense, 5'-GGUGGCUGGAACAGCCAGAUGUGUU-3' (SEQ ID NO: 28), antisense, 5'-AACACAUCUGGCUGUUCCAGCCACC-3' (SEQ ID NO: 29) and Control siRNA sense, 5'-.
The HKP was dissolved in aqueous solution and then mixed with siRNA aqueous solution at N/P ratio of 4:1 by mass, forming nanopplexes of average size of 150-200nm in diameter. Then siRNA-HK-polymer formulation or siRNA, or PBS alone was incorporated into 1.5%

Methylcellulose gel (Sigma). One doze of gel contained 2µg of siRNA or combination of two siRNA alone or in complex with HK polymer.

Wound Measurement

Each wound was digitally photographed twice per week and the wound area was calculated using the Scion Imaging software for Windows (Scion Corp., Frederic, Md.) and expressed as a percentage of the initial wound area.

Histological Evaluation of Wound Healing

To analyze the tissue collagen structure samples were processed by Masson's Trichrome method using Trichrome kit from American MasterTech Scientific Inc. (Lodi, Ca). Stained sections were photographed at magnification 40×, 100× and 400× and assessed for the presence of scar tissue and collagen structure.

Statistical Analysis

Data are presented as mean±SE. A Student's t test was applied to compare the means of samples. A differences were considered statistically significant when P☐0.05.

TABLE 1

| | SiRNA Sequences | |
|---|---|---|
| Lu25-a: | sense 5'-r(GAGGAGCCUUCAGGAUUACAAGAUU)-3' | (SEQ ID NO: 30) |
| | Antisense 5'-r(AAUCUUGUAAUCCUGAAGGCUCCUC)-3' | (SEQ ID NO: 31) |
| CoGFP-1: | sense 5'-r(GCUGACCCUGAAGUUCAUCUGCAUU)-3' | (SEQ ID NO: 32) |
| | Antisense 5'-r(AAUGCAGAUGAACUUCAGGGUCAGC)-3' | (SEQ ID NO: 33) |
| hmTF-25-1: | sense 5'-r(GGAUCCACGAGCCCAAGGGCUACCA)-3' | (SEQ ID NO: 34) |
| | antisense 5'-r(UGGUAGCCCUUGGGCUCGUGGAUCC)-3' | (SEQ ID NO: 35) |
| hmTF-25-2: | sense 5'-r(CCCAAGGGCUACCAUGCCAACUUCU)-3' | (SEQ ID NO: 36) |
| | antisense 5'-r(AGAAGUUGGCAUGGUAGCCCUUGGG)-3' | (SEQ ID NO: 37) |
| hmTF-25-3: | sense 5'-r(GAGCCCAAGGGCUACCAUGCCAACU)-3' | (SEQ ID NO: 38) |
| | antisense 5'-r(AGUUGGCAUGGUAGCCCUUGGGCUC)-3' | (SEQ ID NO: 39) |
| hmTF25-4: | sense, 5'-r(GAUCCACGAGCCCAAGGGCUACCAU)-3' | (SEQ ID NO: 40) |
| | antisense, 5'-r(AUGGUAGCCCUUGGGCUCGUGGAUC)-3' | (SEQ ID NO: 41) |
| hmTF25-5: | sense, 5'-r(CACGAGCCCAAGGGCUACCAUGCCA)-3' | (SEQ ID NO: 42) |
| | antisense, 5'-r(UGGCAUGGUAGCCCUUGGGCUCGUG)-3' | (SEQ ID NO: 43) |
| hmTF25-6: | sense, 5'-r(GAGGUCACCCGCGUGCUAAUGGUGG)-3' | (SEQ ID NO: 44) |
| | antisense, 5'-r(CCACCAUUAGCACGCGGGUGACCUC)-3' | (SEQ ID NO: 45) |
| hmTF25-7: | sense, 5'-r(GUACAACAGCACCCGCGACCGGGUG)-3' | (SEQ ID NO: 46) |
| | antisense, 5'-r(CACCCGGUCGCGGGUGCUGUUGUAC)-3' | (SEQ ID NO: 47) |
| hmTF25-8: | sense, 5'-r(GUGGAUCCACGAGCCCAAGGGCUAC)-3' | (SEQ ID NO: 48) |
| | antisense, 5'-r(GUAGCCCUUGGGCUCGUGGAUCCAC)-3' | (SEQ ID NO: 49) |
| hmCX-25-1: | sense 5'-r(GGUCUGGUGCCUGGUCUGAUGAUGU)-3' | (SEQ ID NO: 50) |
| | antisense 5'-r(ACAUCAUCAGACCAGGCACCAGACC)-3' | (SEQ ID NO: 51) |
| hmCX-25-2: | sense 5'-r(GAGCACCAUUCUCCUUGAAAGGACU)-3' | (SEQ ID NO: 52) |
| | antisense 5'-r(AGUCCUUUCAAGGAGAAUGGUGCUC)-3' | (SEQ ID NO: 53) |
| hmCX-25-3: | sense 5'-r(CCUCAAUUCAGUCUCUCAUCUGCAA)-3' | (SEQ ID NO: 54) |
| | antisense 5'-r(UUGCAGAUGAGAGACUGAAUUGAGG)-3' | (SEQ ID NO: 55) |
| hmCX25-4: | sense, 5'-r(GAUGUUUGCAUUCUUUGCCCAGCAC)-3' | (SEQ ID NO: 56) |
| | antisense, 5'-r(GUGCUGGGCAAAGAAUGCAAACAUC)-3' | (SEQ ID NO: 57) |
| hmCX25-5: | sense, 5'-r(GUCUUUGGUCUGGUGCCUGGUCUGA)-3' | (SEQ ID NO: 58) |
| | antisense, 5'-r(UCAGACCAGGCACCAGACCAAAGAC)-3' | (SEQ ID NO: 59) |
| hmCX25-6: | sense, 5'-r(GUGCCUGGUCUGAUGAUGUAUGCCA)-3' | (SEQ ID NO: 60) |
| | antisense, 5'-r(UGGCAUACAUCAUCAGACCAGGCAC)-3' | (SEQ ID NO: 61) |
| hmCX25-7: | sense, 5'-r(CACCAUUCUCCUUGAAAGGACUUAU)-3' | (SEQ ID NO: 62) |
| | antisense, 5'-r(AUAAGUCCUUUCAAGGAGAAUGGUG)-3' | (SEQ ID NO: 63) |

TABLE 1-continued

SiRNA Sequences

| | | |
|---|---|---|
| hmCX25-8: | sense, 5'-r(CAAUUCAGUCUCUCAUCUGCAAUAA)-3' | (SEQ ID NO: 64) |
| | antisense, 5'-r(UUAUUGCAGAUGAGAGACUGAAUUG)-3' | (SEQ ID NO: 65) |
| hmHX-25-1: | sense 5'-r(GGUGGCUGGAACAGCCAGAUGUGUU)-3' | (SEQ ID NO: 66) |
| | antisense 5'-r(AACACAUCUGGCUGUUCCAGCCACC)-3' | (SEQ ID NO: 67) |
| hmHX-25-2: | sense 5'-r(GCUGGAACAGCCAGAUGUGUUGCCA)-3' | (SEQ ID NO: 68) |
| | antisense 5'-r(UGGCAACACAUCUGGCUGUUCCAGC)-3' | (SEQ ID NO: 69) |
| hmHX-25-3: | sense 5'-r(CGCCAGAUUACCAUCUGGUUUCAGA)-3' | (SEQ ID NO: 70) |
| | antisense 5'-r(UCUGAAACCAGAUGGUAAUCUGGCG)-3' | (SEQ ID NO: 71) |
| hmHX25-4: | sense, 5'-r(GGAGCCCGGCAAUUAUGCCACCUUG)-3' | (SEQ ID NO: 72) |
| | antisense, 5'-r(CAAGGUGGCAUAAUUGCCGGGCUCC)-3' | (SEQ ID NO: 73) |
| hmHX25-5: | sense, 5'-r(CAAGGAUAUCGAAGGCUUGCUGGGA)-3' | (SEQ ID NO: 74) |
| | antisense, 5'-r(UCCCAGCAAGCCUUCGAUAUCCUUG)-3' | (SEQ ID NO: 75) |
| hmHX25-6: | sense, 5'-r(GGACAAGAGGCGCAAGAUCUCGGCA)-3' | (SEQ ID NO: 76) |
| | antisense, 5'-r(UGCCGAGAUCUUGCGCCUCUUGUCC)-3' | (SEQ ID NO: 77) |
| hmHX25-7: | sense, 5'-r(GCAAGAUCUCGGCAGCCACCAGCCU)-3' | (SEQ ID NO: 78) |
| | antisense, 5'-r(AGGCUGGUGGCUGCCGAGAUCUUGC)-3' | (SEQ ID NO: 79) |
| hmHX25-8: | sense, 5'-r(CCAUCUGGUUUCAGAACCGCCGGGU)-3' | (SEQ ID NO: 80) |
| | antisense, 5'-r(ACCCGGCGGUUCUGAAACCAGAUGG)-3' | (SEQ ID NO: 81) |

Where the sequences Lu25-a and CoGFP-1 are the control siRNA duplexes for in vitro and in vivo testing. The sequences hmTF-25-2, hmCX-25-1 and hmHX-25-1 have been selected to target TGFβ1, Cox-2 and Hoxb13 genes from the total of 24 siRNA sequences, based on their silencing activities in the cell culture screening. Among those 24 siRNA sequences, except hmTF25-7, all have potent gene silencing activities.

Example 1

Selection of Potent siRNA Duplexes Targeting TGFβ1, Cox-2 and Hoxb13

We used 25 mer blunt-ended siRNA duplexes due their active and durable potencies then 21 mer siRNA duplexes. Each sequence is able to target both human and mouse corresponding gene. Before testing those siRNA oligos (synthesized by Qiagen) in the corresponding cells, a human PC-3 cell was used simply because that the three targets expressing from this cell (FIG. 1). The most potent siRNA duplex against each target was selected for TGFβ1, COX-2 and HoxB13.

Total RNA from each of those transfected cell lines including HoxB13 (mouse) expressing REK cells, COX-2 (human) expressing cells and mouse embryonic endothelial cells are isolated and purified for RT-PCR analysis. The PCR products should be loaded on a 1% agarose gel and stained with ethidium bromide. The PCR product should exhibit the levels of the knockdown of each particular mRNA using the particular siRNA duplexes. The result from this experiment is to determine the potency of each siRNA duplex and provide the first look if a particular siRNA duplex should be the most potent one. The RT-PCR analysis is closely coordinated with the transfection experiment so that proper conditions are optimized for efficient transfection for particular cell line, in order to achieve sufficient amount of total RNA for the PCR analysis. In addition, the selection of the most potent siRNA duplex for each gene should be based on three repeated experiments. The sample normalization was done with a 361bp fragment of a house keeping gene rig/S15. The selected sequences were listed below: (1) hmTF-2: sense, 5'-CCCAAGGGCUACCAUGCCAACUUCU-3' (SEQ ID NO: 36), antisense, 5'-AGAAGUUGGCAUG-GUAGCCCUUGGG-3' (SEQ ID NO: 37); (2) hmCX-1: sense, 5'-GGUCUGGUGCCUGGUCUGAUGAUGU-3' (SEQ ID NO: 50), antisense, 5'-ACAUCAUCAGACCAG-GCACCAGACC-3' (SEQ ID NO: 51); (3) hmHX-1: sense, 5'-GGUGGCUGGAACAGCCAGAUGUGUU-3' (SEQ ID NO: 66), antisense, 5'-AACACAUCUGGCUGUUCCAGC-CACC-3' (SEQ ID NO: 67).

Example 2

Potent siRNA was Validated in both Human and Mouse Cells

We also surveyed the expressions of these three genes in the mouse C166 cell. Eight siRNA duplexes for each targeted were screened by siRNA transfections followed by total RNA isolation and Q-RT-PCR. Demonstrated in FIG. 2, the potent siRNA selected for targeting TGFβ1 has the same activity in both human and mouse cells. The Q-PCR primers were used for targeting TGFβ1, Cox-2 and Hoxb13 genes from both human and mouse cells. Human TGFβ1 primers: Forward -5'GAGCCTGAGGCCGACTACTA-3' (SEQ ID NO: 14), Reverse-5'-CGGAGCTCTGATGTGTTGAA (SEQ ID NO: 15); Product Size: 131. Human Cox-2 primer: Forward 5'-ATTCCCTTCCTTCGAAATGC-3' (SEQ ID NO: 16), Reverse 5'-GGGGATCAGGGATGAACTTT-3' (SEQ ID NO: 17); Product Size: 262. Human Hoxb13 primer: Forward 5'-ACCATCTGGTTTCAGAACCG-3' (SEQ ID NO: 82), Reverse 5'-CTCCTGAGGAACAGTC-CAGC-3' (SEQ ID NO: 83); Product Size: 230. Mouse TGFβ1 primer: Forward 5' GTGCGGCAGCTGTACATT-GACTTT-3' (SEQ ID NO: 6), Reverse 5' TGTGTTGGTT-GTAGAGGGCAAGGA-3' (SEQ ID NO: 7); Product Size: 127. Mouse Cox-2 primer: Forward 5'-ACTGGGCCATG- GAGTGGACTTAAA-3' (SEQ ID NO: 8), Reverse 5'-AACTGCAGGTTCTCAGGGATGTGA-3' (SEQ ID NO: 9); Product Size: 186. Mouse Hoxb13 primer: Forward 5'-ATGGCCAGTTACCTGGATGTGTCT-3' (SEQ ID NO: 10), Reverse 5'-AGAATGGACCTGGTGGGTTCTGTT-3' (SEQ ID NO: 11); Product Size: 102.

Example 3

Established a Skin Excision Wound Model

Figure 2:
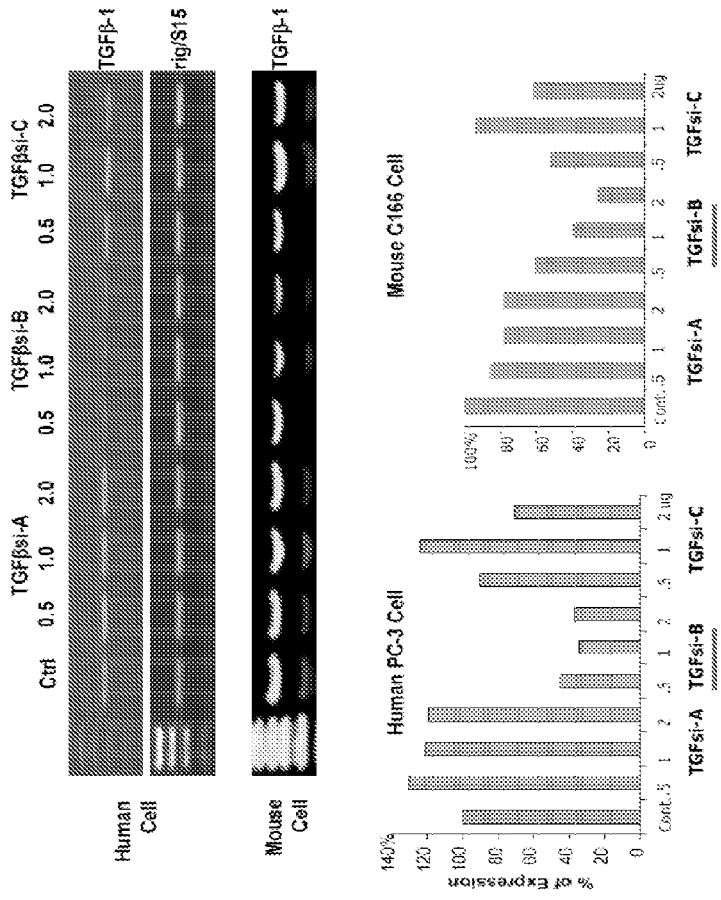
FIG. 2. Human and Mouse Homologues siRNAs. TGFβ1 was used as the example to demonstrate the selected siRNA having gene silencing activities in both Human and Mouse cells. The gene silencing activities can be distinguish from human TGFβ1 knockdown (PC-3 cells) and mouse TGFβ1 knockdown (C166 cells) using quantitative RT-PCR. Rig/S15 was used as a control.
Figure 3:
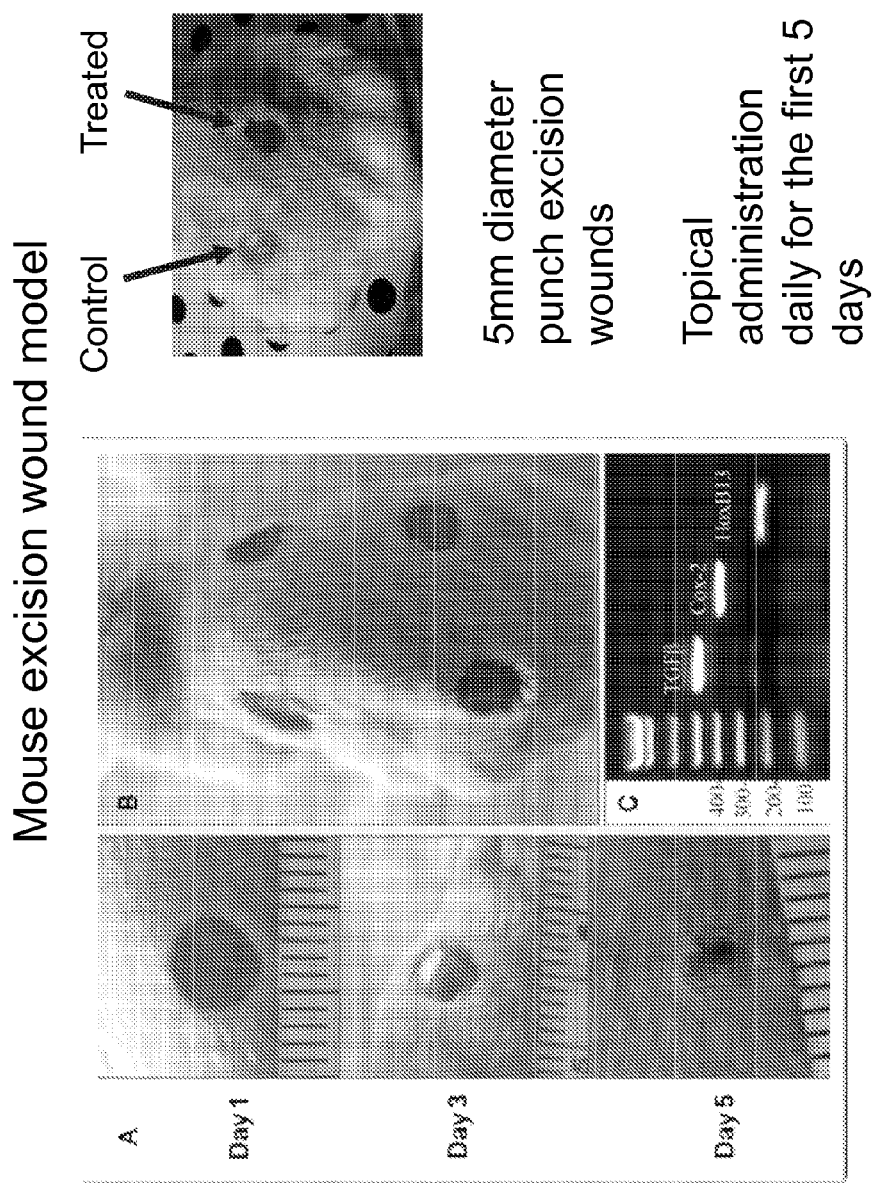
FIG. 3. Defining Mouse Skin Excision Wound Model. The mouse skin excision wound model was established with the circler punch (5 mm diameter). The PCR analysis was used to detect expression of TGFβ1, Cox-2 and Hoxb13 in the mouse skin tissues, with primers targeting both human and mouse genes. The same primers were used for target gene knockdown in both human and mouse cells. The siRNA therapeutics were topically administrated on the wounds daily for the first 5 days.

Six to eight week old Balb/c mice (Taconic, NY) were used for establishing a skin excision wound model. A paired 5 mm diameter full-thickness excision skin wounds were created on both sides of the dorsal midline the depilitated dorsum of each mouse (FIG. 2). The control and treated wounds can be observed for wound healing phenotype such as changes of wound closure and target gene knockdown and histopathological changes. In order to evaluate the siRNA-mediated gene expression knockdown in the mouse skin tissue, we use RT-PCR to detect mRNA expressions of TGF-β, Cox-2 and Hoxb13 in the mouse skin total RNA samples (FIG. 3). Total RNA samples were extracted from skin samples according to the manufacture's instructions (RNAqueous-4PCR, Ambion). 0.25µg of total RNA was incubated at 70° C. for 3 min with oligo (dT) primers and then reverse-transcribed at 42° C. for 30 min in 20µl reaction mixture containing reverse transcriptase followed by PCR (35cycles) using specific primers for TGF-β, Cox-2 and HoxB13 genes. (1) Mouse TGF-β, forward: 5'-CTACTGT-GTGCTGAGCACCTT-3' (SEQ ID NO: 1), reverse: 5'-CGCTGCTCGGCCACTCTGGCT-3' (SEQ ID NO: 2), and product: 488bp; (2) Mouse Cox-2,forward:5'-GGAAGCCTTCTCCAACCTCT-3' (SEQ ID NO: 3), reverse: 5'-GGATACACCTCTCCACCAAT-3' (SEQ ID NO: 4), product: 371bp; (3) Mouse HoxB13, forward 5'-CTCCAGCTCCTGTGCCTTAT-3' (SEQ ID NO: 51, reverse: 5'-ACTGGCCATAGGCTGGTATG-3' (SEQ ID NO: 84), product: 205bp.

Example 4

HKP for siRNA Delivery

Figure 4:
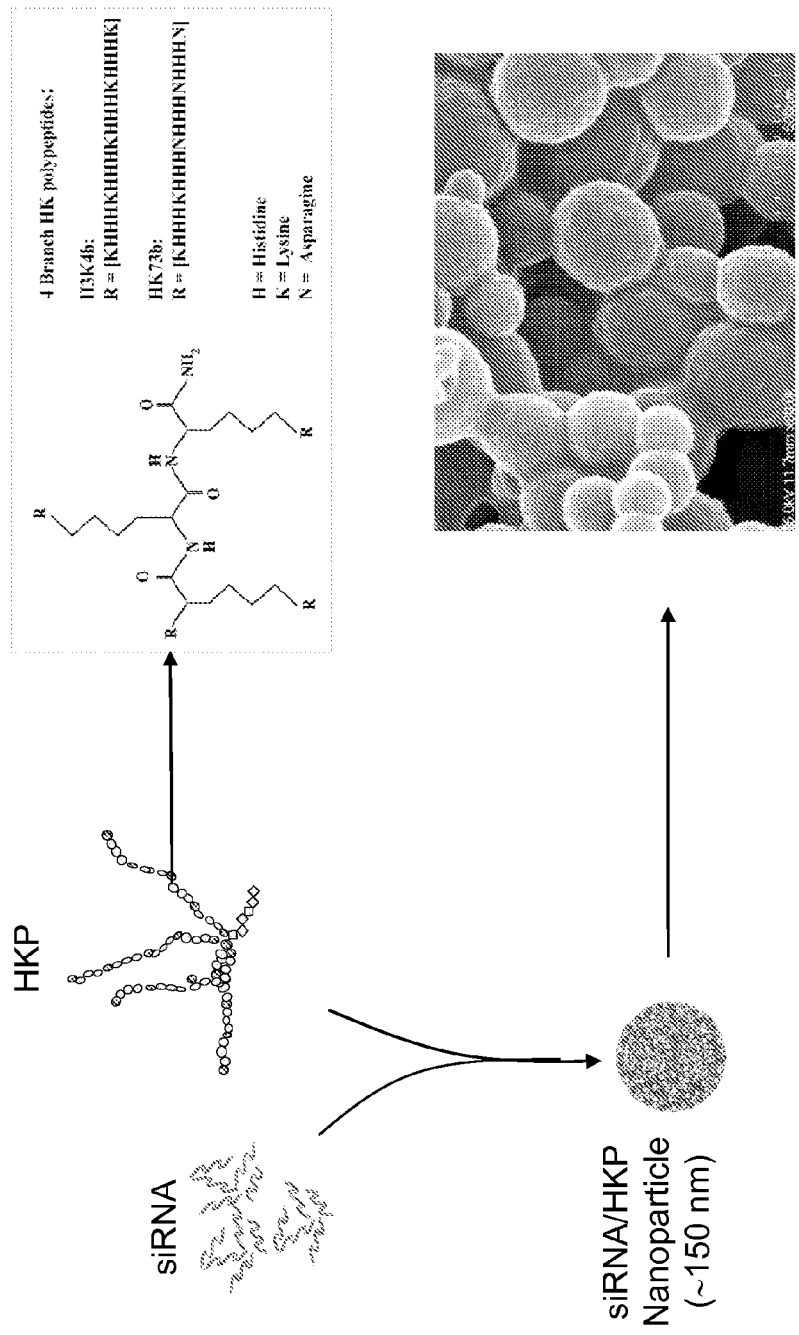
FIG. 4. Selection of HK polymer. The Histidine-Lysine polymer was selected for topical delivery of siRNA onto the excision skin wound. The HK polymer (two species: H3K4b, HK73) aqueous solution and siRNA aqueous solution mixture has resulted in nanoparticle with average size of 150 nm, illustrated in the SEM image. The N:P ratio is about 4:1.

Optimized histidine-lysine polymers (HKP) have been applied for siRNA deliveries in vitro and in vivo. A pair of the HK polymer species, H3K4b and PT73, has a Lysine backbone with four branches containing multiple repeats of Histidine, Lysine or Asparagine. When this HKP aqueous solution was mixed with siRNA at a N/P ratio of 4:1 by mass, the nanoparticles (average size of 100-200 nm in diameter) were self-assembled (FIG. 3). Optimal branched histidine-lysine polymer, HKP, was synthesized on a Ranin Voyager synthesizer (PTI, Tucson, Ariz.). The two species of the HKP used in the study were H3K4b and PT73 with a structure of (R)K(R)-K(R)—(R)K(X), for H3K4b where R=KHHHKHHHKHHHKHHHK; and for PT73 where R=KHHHKHHHNHHHNHHHN, X=C(O)NH2, K=lysine, H=histidine and N=Asparagine. The HKP was dissolved in aqueous solution and then mixed with siRNA aqueous solution at a ratio of 4:1 by mass, forming nanoparticles of average size of 150-200 nm in diameter. The HKP-siRNA aqueous solution was semi-transparent without noticeable aggregation of precipitate, and can be stored at 4° C. for at least three months. We applied both H3K4b and PT73 for skin wound siRNA delivery in the preliminary study and will test both in the proposed studies (FIG. 4).

Example 5

HK Polymer for Wound Site siRNA Delivery

Figure 5:
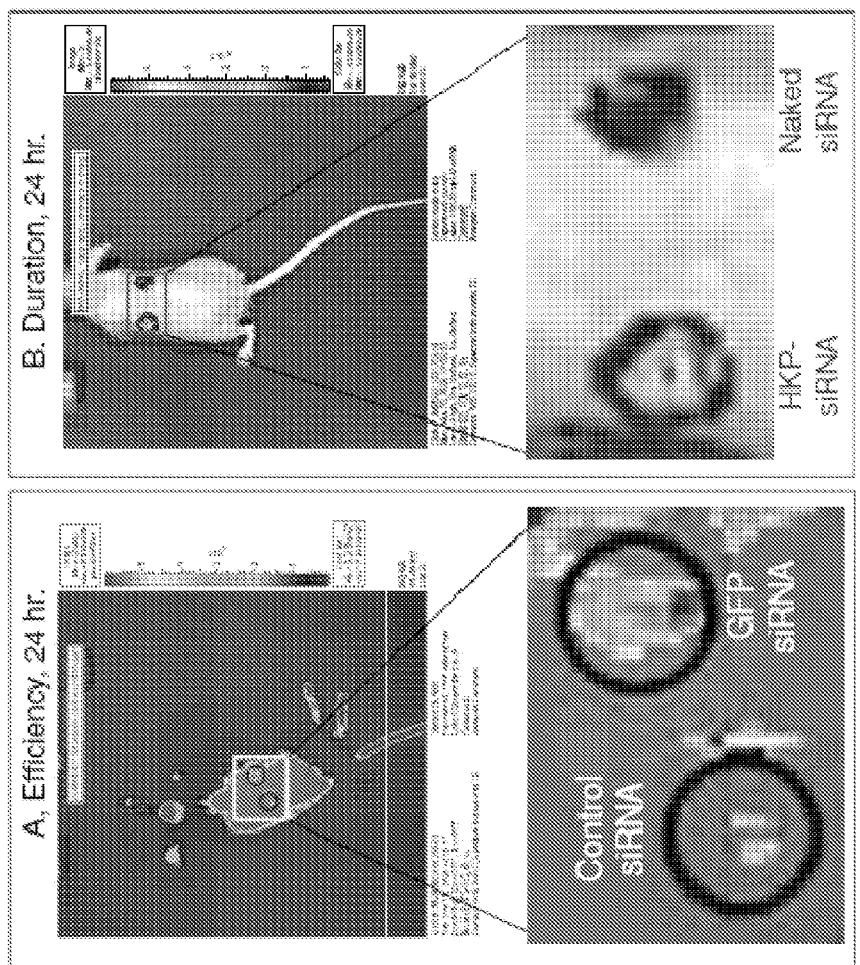
FIG. 5. Efficiency and Duration of HKP-siRNA nanoparticle for Skin Wound Delivery. A. HKP-siRNA targeting GFP was able to silence wound site GFP expression for 24 hours. B. HKP-siRNA (labeled) was able to sustain for 24 hrs after subcutaneous injection.

The optimized histidine-lysine polymers (HKP) have been applied for siRNA deliveries in vitro and in vivo. One HK polymer species, H3K4b, having a Lysine backbone with four branches containing multiple repeats of Histidine and Lysine, was used for packaging siRNA with a N/P ratio of 4:1 by mass. The nanoparticles (average size of 150 nm in diameter) were self-assembled. To evaluate the HKP-mediated siRNA topical delivery onto the skin wound site, we used a GFP mouse model with formulated HKP-siRNA nanoparticle for wound site gene knockdown (FIG. 5A). The HKP-siRNA$_{GFP}$ reduced GFP expression significantly by approximately 80%, comparing to the HKP-siRNA (control) in this mouse model. The second animal model we used was athymic nude mice (NCI Frederick) (FIG. 5B) with subcutaneous injection of HKP/siRNA (Fluorescence labeled). Twenty-hours later, HKP packaged siRNA preserved a much higher intensity on the injection site.

Example 6

Identify the Appropriate Dosage for Topical siRNA Delivery

Figure 6:
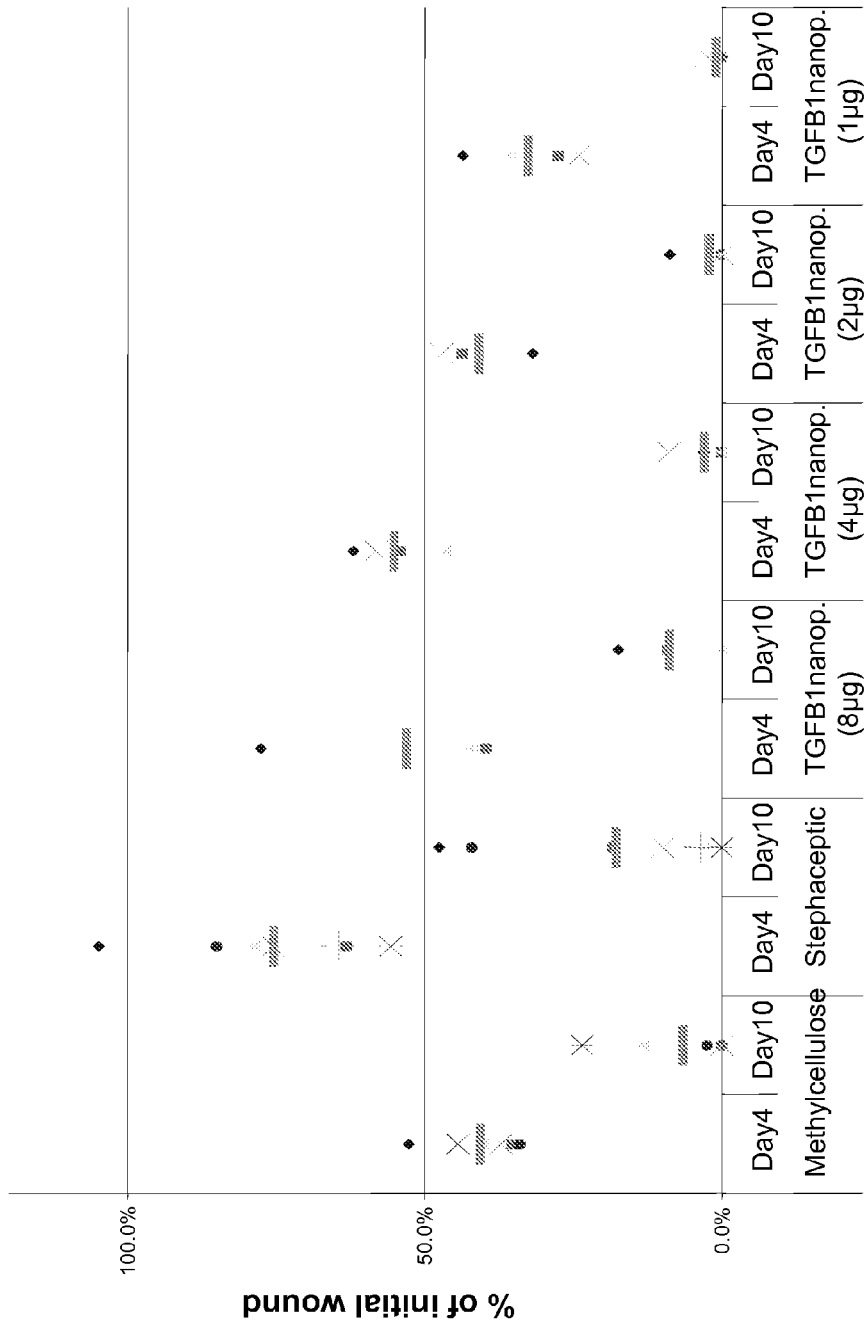
FIG. 6. Comparison of Different Dosage Effects Selection of proper dosage for topical siRNA delivery on the excision skin wound. Various dosages of TGFβ1 siRNA (1 µg, 2 µg, 4 µg and 8 µg) were formulated in 50 µl of 1.5% methylcellulose gel for topical delivery of siRNA onto the 5 mm circler punch wound site. The treatment was administrated with regimens of daily for the first 5 days. The wound closure speeds for each treatment were observed. The fast closure was observed for 1 µg and 2 µg dosage.

HKP-TGFβ1 nanoparticle was used for evaluation of the dosage needed for the topical delivery on the wound site. Four different dosages, 8, 4, 2, 1 µg, were tested for improvement of wound closure rate in comparison with methycellulose only or Stephaceptic only. In this case, the dosages of 2 and 1 µg were more effective than the higher dosages for speedy wound closure at day 10. Therefore, we selected the 2 µg and 1 µg for the future application on the mouse animal models (FIG. 6).

Example 7

Quantification of Wound Closures after Treatments

Figure 7:
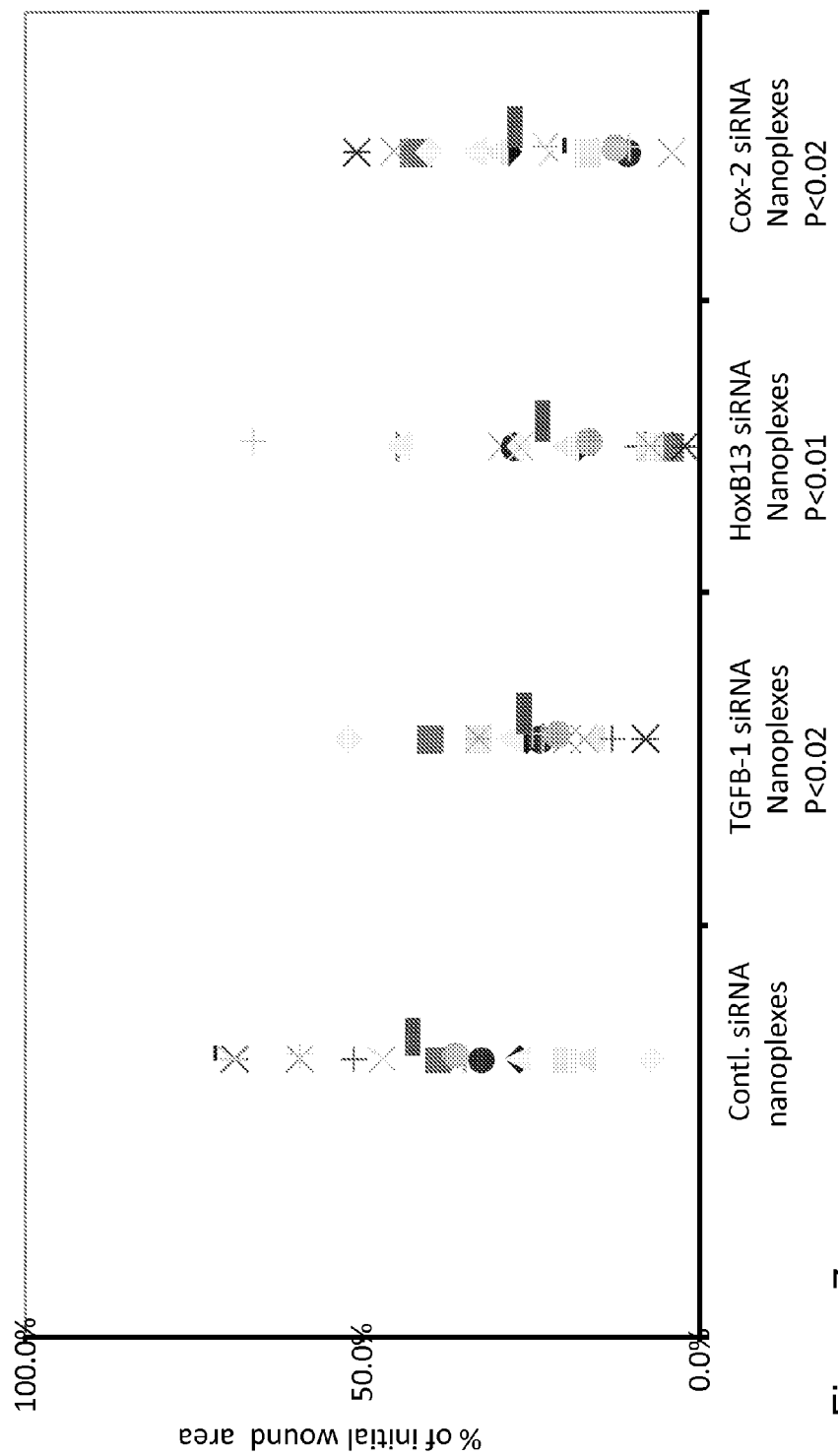
FIG. 7. All Three Selected Targets Showed Efficacy. The potent siRNA duplexes selected from the in vitro gene knockdown experiments targeting TGFβ1, Cox-2 and Hoxb13 respectively, were tested for the therapeutic benefit for accelerated excision wound closure. All those potent siRNA duplexes were able to demonstrate significant therapeutic efficacy as shown in the figure.

The next experiment we did was to quantify the wound closure at each time point. At same time, we also asked if the therapeutic benefit is the result of HK polymer or siRNA itself. Four groups under different treatments with 10 samples each were conducted in the study: 1) Methylcellulose only, 2) Methylcellulose plus HKP-siRNA TGFβ-1, 3) Methylcellulose plus naked siRNA$_{TGFβ-1}$, and 4) Methylcellulose plus HKP-siRNA$_{control}$. The daily treatment was applied for the first 5 days. The wound images were collected at day 5 and day 9, and further quantified using Scion Imaging Program for Windows (Scion Corp., Frederic, Md.) and presented with a percentage of the initial wound area. By averaging the measurements of the wound samples of each group on day $5^{th}$ and $9^{th}$ (FIG. 7). we found significant differences (P<0.05) between group 2 and other three groups, although some effects were seen with group 3. The therapeutic benefit for faster skin wound closure is the result of HKP-siRNA$_{TGFβ-1}$.

Example 8

Histopathology Data Showed Improved Wound Healing for all Three Targets

Figure 8:
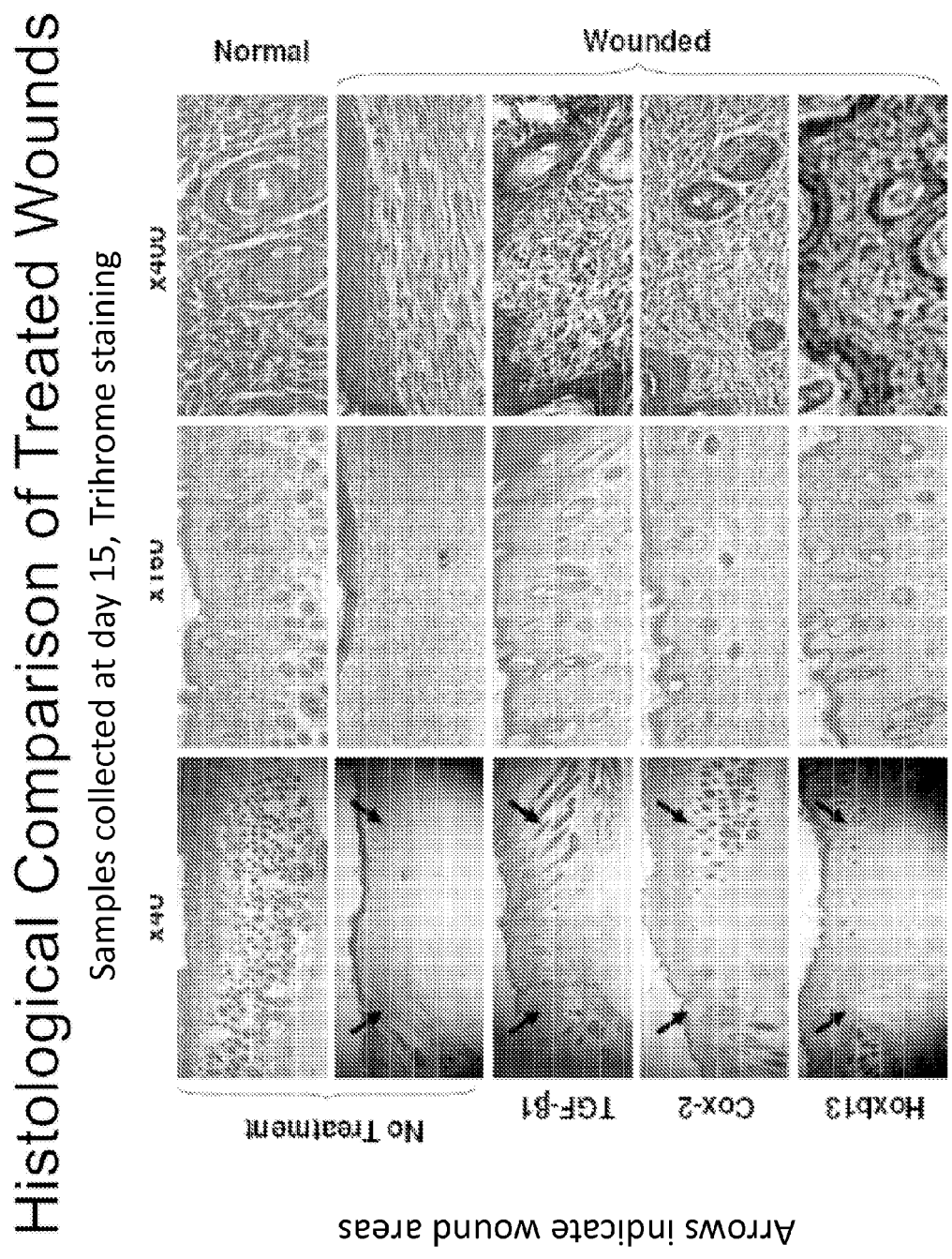
FIG. 8. Histological Comparison of Treated Wounds. Trichrome staining on the tissue samples collected from the each treatment group The texture of TGFβ1, Cox-2 and Hoxb13 siRNA treated wounds is very much like the normal skin but not the untreated wound tissue. This result reflects the minimized scar formation on the skin wound sites.

Based on the benefit we observed with silencing TGFβ1 and Cox-2 in the skin wound healing process, we further looked into the possible effect of Hoxb13 knockdown using the same mouse model Skin samples were harvested 14 days after wounding, paraformaldehyde-fixed and subjected to Masson's trichrom staining to detect collagenous scar tissue. Restoration of the normal tissue architecture can be seen in wounds treated with HKP packaged TGFβ1 siRNA-, Cox-2 siRNA- and Hoxb13 siRNA nanoplexes. Three different magnifications (×40, ×160 and ×400) were used to demonstrate the dermal tissue structure surrounding the wounded area as indicated with arrows. The architecture of the neodermis of wounds treated with TGFβ1 siRNA-, Cox-2 siRNA-, and Hoxb13 siRNA-nanoplexes resembles that of normal dermis with the reticulate collagen fibers loosely arranged in the basket weave pattern. By contrast, the collagen fibers in the neodermis of sham control wounds and control siRNA-nanoplexes treated wounds are densely placed in an abnormal parallel pattern. These events allow collagen fibers to lie closer together (FIG. 8), facilitating collagen cross-linking and ultimately decreasing scar thickness. Intramolecular and intermolecular collagen cross-links result in increased wound bursting strength.

Example 9

Combination of siRNA Duplexes to Enhances Wound Closure

Figure 9:
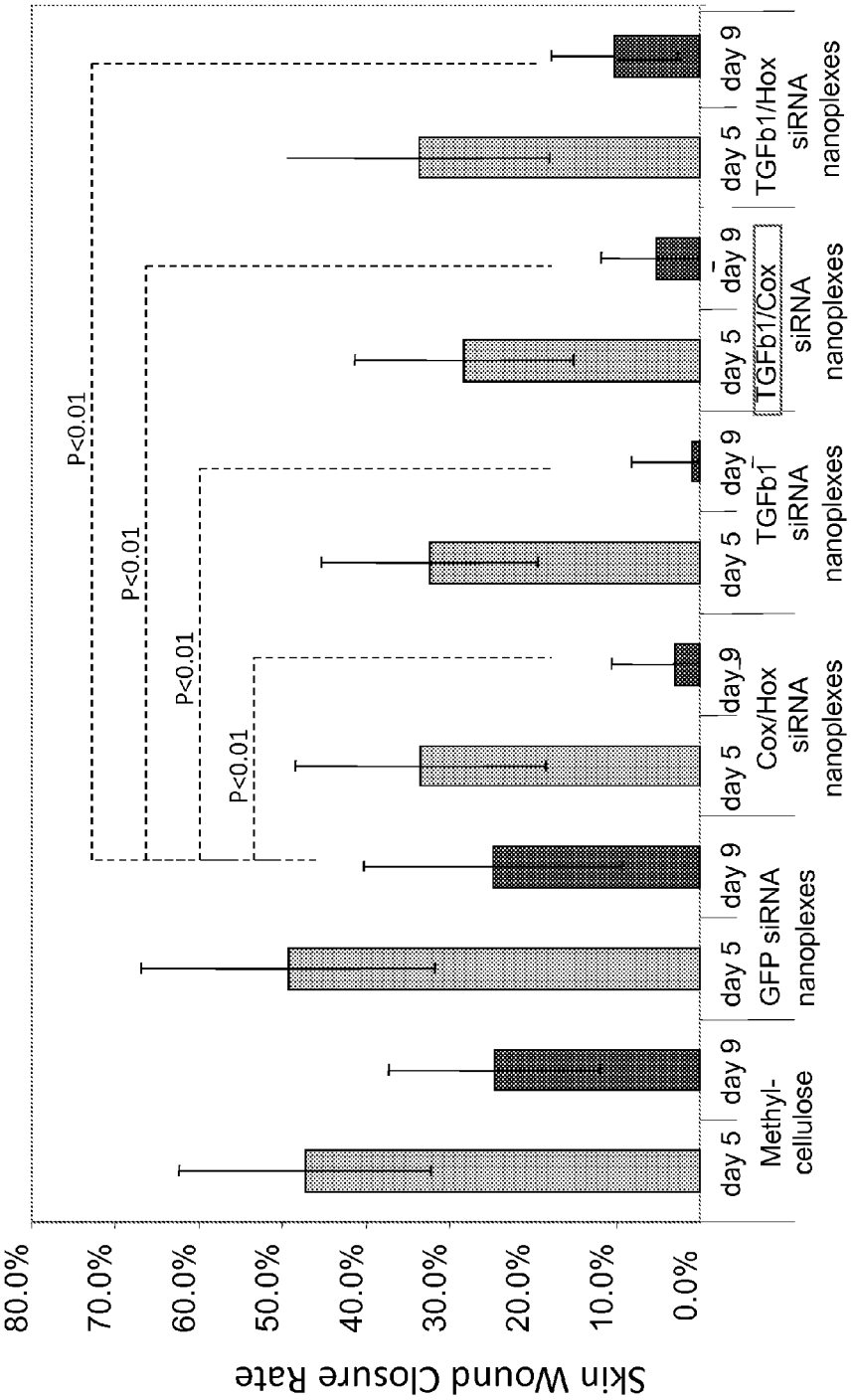
FIG. 9. Benefit of Combined siRNA Formulations. The siRNA duplexes pairs were used for evaluation of the therapeutic benefit for accelerated wound closure. The TGFβ1 siRNA was used as a control. Interestingly, TGFβ1 and Cox-2 combination provided the fastest wound closure on day 5. There are no significant differences among different treatment groups in terms of wound closure time.

In order to evaluate the synergistic effect of combining potent siRNA duplexes in a cocktail, we tested them in pairs and see if two potent siRNA duplexes (targeting its own target specifically) packaged in HKP nanoparticle will have better results in wound closure and skin wound histopathological response. Three pairs of siRNA duplexes, TGFβ+Cox-2, TGFβ+Hoxb13 and Cox-2+Hoxb13 packaged in HKP, were used with 1.5% methylcellulose gel on the excision wound areas of Balb/c model. Both the target gene knockdown (data not shown) and wound closure (FIG. 9) were evaluated. In terms of wound closure on both day 5 and day 9 after treatments, all pairs exhibited the potent activity similar to the TGFβ1-siRNA, while the pair TGFβ1-Cox-2 siRNA pair demonstrated stronger benefit for wound closure at day 5.

Example 10

Combination of siRNA Duplexes Resulted in Normal Skin Like Structure

Figure 10:
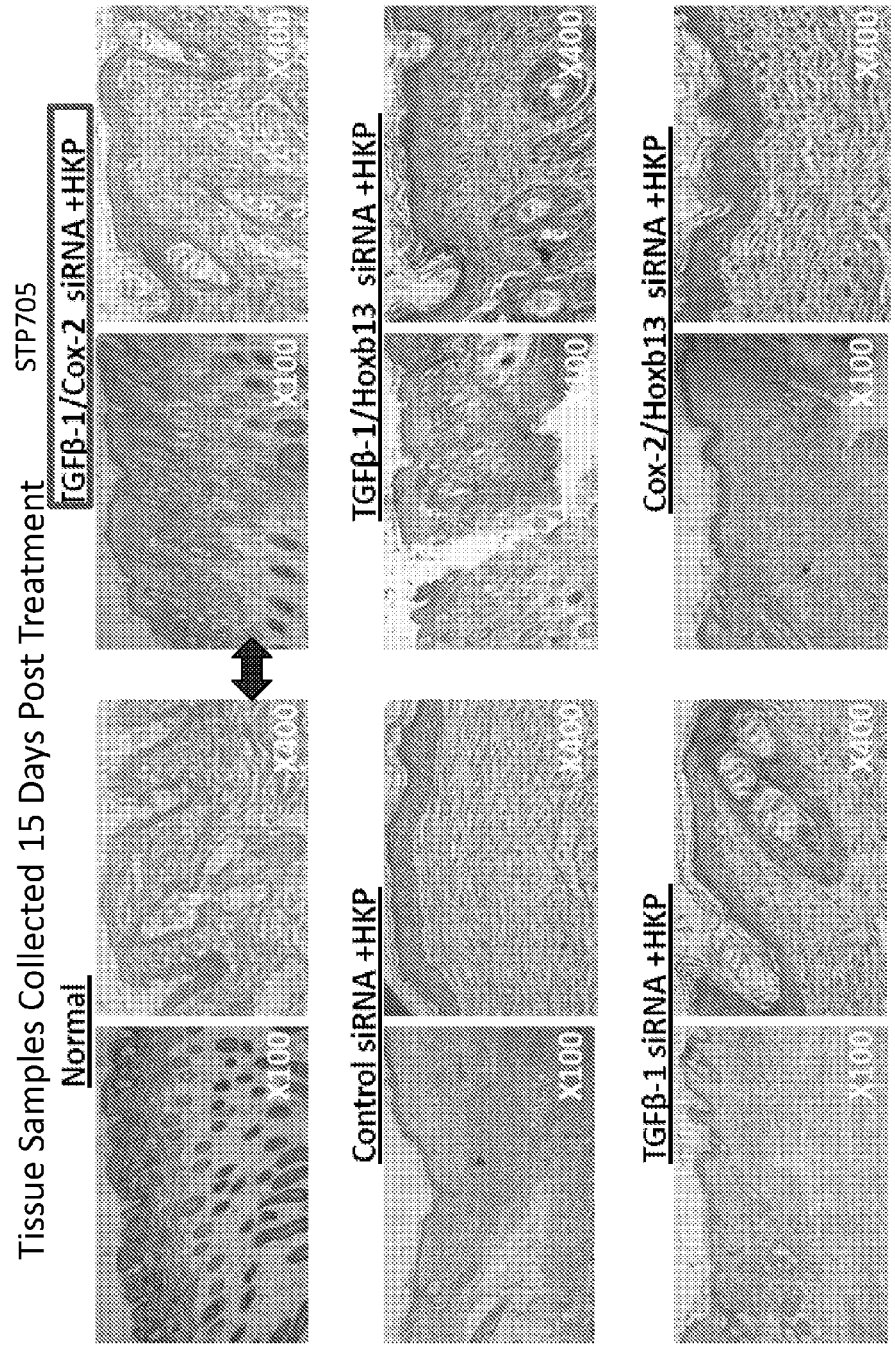
FIG. 10. TGFβ1/Cox-2 siRNA Combination is the Best. The experiment results demonstrated potent activity of combined siRNA therapeutic activities, especially, the TGFβ1-Cox-2 combination illustrated a normal tissue like texture after 5 repeated daily. The tissue samples were collected on the 15 days post treatment. The formulation of TGFβ1-Cox-2 siRNA and HK polymer achieved the most potent therapeutic benefit among the controls and three combinations. Therefore, we identified and selected TGFβ1-Cox-2 combination as STP705.

To our surprise, the TGFβ1-Cox-2 pair again demonstrated a normal skin tissue like texture from the tissue samples collected 15 days after the treatment (FIG. 10). We have identified a pair of siRNA targeting both TGFβ1 and Cox-2 representing the strongest agent (STP705) for the siRNA based therapeutics for accelerated wound closure with less scar formation. This STP705 formulation is comprised of one siRNA duplex targeting TGFβ1 (homology to human, mouse and pig genes) and one siRNA duplex targeting Cox-2 (homology to human, mouse and pig genes), which are packaged by the Histidine and Lysine branched polymer to form nanoparticle in diameter of 150 nm in average. The nanoparticle formulation was in 1.5% methylcellulose aqueous solution. The STP705 formulation is applied topically once a day and resulted in significant therapeutic benefit for skin scarless wound healing. The following sequences (hmTF-25-2 and hmCX-25-1) are currently used as a component of STP705:

hmTF-25-2:
(SEQ ID NO: 36)
sense 5'-r(CCCAAGGGCUACCAUGCCAACUUCU)-3'

(SEQ ID NO: 37)
antisense 5'-r(AGAAGUUGGCAUGGUAGCCCUUGGG)-3' which has 100% homology with following sequences:
XM_512687, *Pan troglodytes* (chimpanzee) transforming growth factor, beta 1
DQ787012, *Canis familiaris* (dog) transforming growth factor beta 1
XM_001100842, *Macaca mulatta* (monkey) transforming growth factor bet a 1
NM_021578, *Rattus norvegicus* (Rat) transforming growth factor, beta 1
BC013738, *Mus musculus* (mouse) transforming growth factor, beta 1
NM_001173023, *Cavia porcellus* (Guinea pig) transforming growth factor, beta 1
XM_002722312, *Oryctolagus cuniculus* (Rabbit) transforming growth factor, beta 1
Except: X12373, *Sus scrofa* (Porcine) transforming growth factor-beta 1, there is one point mutation (CCCAAGGGCTACCATGCCAATTTCT) (SEQ ID NO: 85).

hmCX-25-1:
(SEQ ID NO: 50)
sense 5'-r(GGUCUGGUGCCUGGUCUGAUGAUGU)-3'

(SEQ ID NO: 51)
antisense 5'-r(ACAUCAUCAGACCAGGCACCAGACC)-3' which has 100% homology with following sequences:
AY065644, *Sigmodon hispidus* (cotton rat) prostaglandin H synthase 2 (COX2)
AF207824, *Sus scrofa* (pig) cyclooxygenase-2 (COX-2)
AF031699, *Bos Taurus* (cow) prostaglandin G/H synthase-2 (PGHS-2) gene
OAU68486, *Ovis aries* (sheep) prostaglandin H synthase-2 PGHS-2) mRNA
EF036473, *Felis catus* (cat) cyclooxygenase 2 mRNA
XM_524999, *Pan troglodytes* (chimpanzee) prostaglandin-endoperoxide synthase 2
AY044905, *Canis familiaris* (dog) prostaglandin G/H synthase-2 mRNA In addition, we saw that the combination of siRNA duplexes hmTF-25-2 and hmHX-25-1 also demonstrated efficacy for the normal skin like structure (FIG. 10), even though the activity was not as potent as that of hmTF-25-2 and hmCX-25-1 combination.

hmHX-25-1:
(SEQ ID NO: 66)
sense 5'-r(GGUGGCUGGAACAGCCAGAUGUGUU)-3'

(SEQ ID NO: 67)
antisense 5'-r(AACACAUCUGGCUGUUCCAGCCACC)-3'

Example 11

Pig Skin Full Thickness Excision Wound Model

Figure 11:
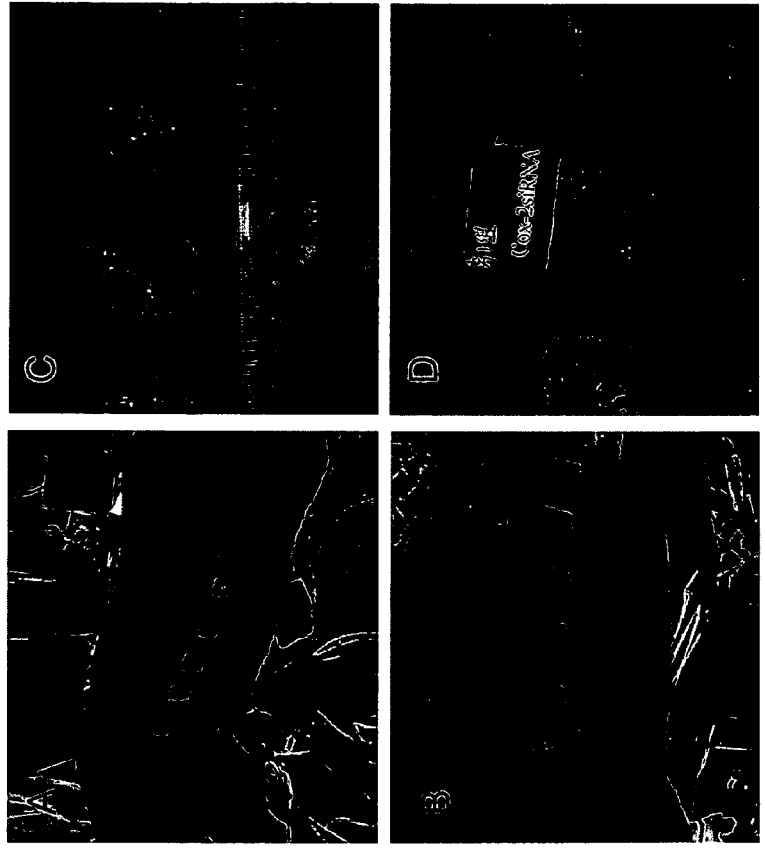
FIG. 11. The Pig Skin Excision Wound Model. The pig skin is more like the human skin in terms of structure and scar formation The potent siRNA duplexes we selected having 100% sequence homology to swine TGFβ1 and Cox-2 targets. A: group one; B: group two; C: The skin wound size is about 2×2 cm. The electric surgical knife was used for creating the excision wound model. D: daily topical administration with STP-705 formulation (Methylcellulose+HKP-siRNA nanoparticles) onto the skin excision wounds.

An ordinary domestic female piglet (Taihuzhu) of 15 kg in weight was anaesthetized with pentobarbital sodium at 40 mg/kg through ear vein injection. And respirator was applied for breath assistance. The piglet was put on operation desk in supine position, and hairs were shaved off the back after sanitized with iodophor solution (1% w/v). A full thickness skin wound was produced along the marked lines with an electric scalper (FIG. 11). Experimental agents (formulated in HKP polymer and methylcellulose) were then applied to the wounds according to design daily for total of 9 days. Afterwards pictures were taken twice weekly to track changes. Biopsy samples were taken for pathology and IHC studies 30-47 days after the initial wounding.

Example 12

STP705 is Effective on Pig Skin Excision Wound Model

Figure 12:
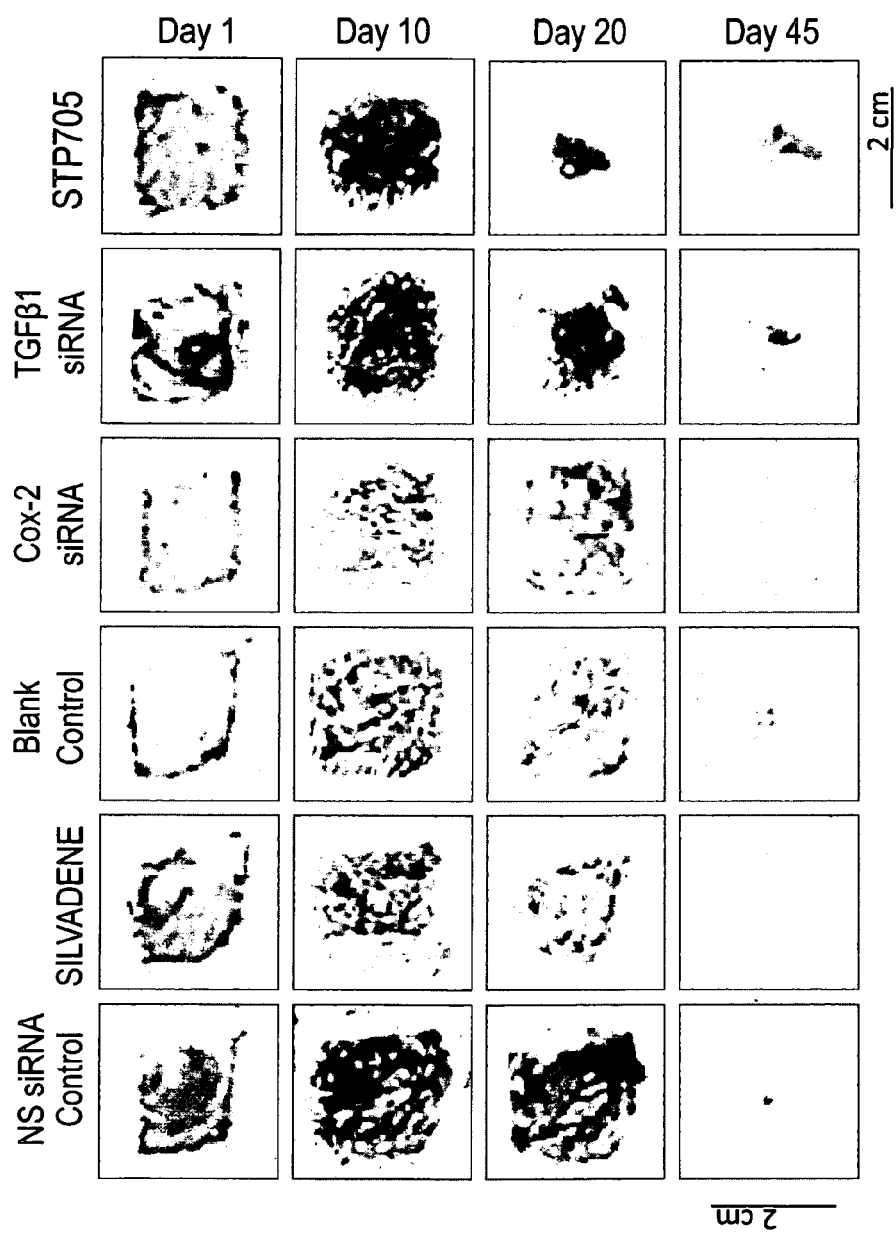
FIG. 12. STP705 Accelerates Pig Skin Wound Closure. The pig skin excision wounds were treated with six groups: non-related siRNA sequence control, Silverdene, carrier only, Cox-2 siRNA only, TGF β1 only and STP705. On the day 20 post treatment, the STP705 treated wound was showing a significantly better healing than others. On day 45, STP705 treated wound almost fully covered by hair vs. Silverdene treatment with markable scar.

The pig skin wound models have been widely accepted as the most appropriated in vivo system for evaluation of skin scarless wound healing of human skin, largely due to their similar physiological and histological properties. The potent siRNA duplexes targeting either TGFβ1 or Cox-2 and with homology to both human and mouse are also homologous to the same genes in pig. Therefore, the same HKP Nanoparticle/siRNA formulation was tested on a pig skin excision wound model. A 35 pounds pig was used for the study. Wounds were established (2×2 cm$^2$) and treated using the methylcellulose-HKP-siRNA nanoparticles cream and controls: (1) non-related siRNA; (2) positive control drugs used in the local hospital; (3) no treatment; (4) TGFβ1-siRNA; (5) Cox-2-siRNA and (6) combination of TGFβ1 and Cox-2 siRNAs. The wounds were treated daily for the first 15 days and the animal behavior and wound appearances were observed daily. This animal study was carried out with the standard protocols approved by the IACUC committee of Suzhou University (FIG. 12). Three different treatments were applied for the corresponding wounds using topical administration for 15 days (daily). The animal wounds were examined daily and the images on day 10, 20 and 45 are illustrated. Started from day 20, the remarkable difference of wound closures between STP705 treated and others can be seen. On day 30, hair growth was observed and on day 45 the wound almost completely healed after STP705 treatment. The histology analyses (day 47) showed clearly normalized tissue structure in the STP705 treated wound comparing the partial normalized and scaring tissues of other wounds with or without treatments (FIG. 12).

Example 13

Histological Analysis for Anti-Scar Effect of STP705 on Pig Skin Wound

The tissue samples were collected from each wound site for histological analyses of the therapeutic benefit of STP705 on the pig skin excision wound model. The Trichrome staining was used. In addition to the samples from the following groups: (1) non-related siRNA; (2) positive control drugs used in the local hospital; (3) no treatment; (4) TGFβ1-siRNA; (5) Cox-2-siRNA and (6) combination of TGFβ1 and Cox-2 siRNAs, the normal tissue also was used to compare the treatment results. With 4 different magnifications, ×40, ×100, ×200 and ×400, the comparisons were made to observe the differences among groups. Clearly the textures of STP705 treated tissue samples are very much like the normal tissue's texture, verses the scar tissue like textures from other control groups.

Figure 13:
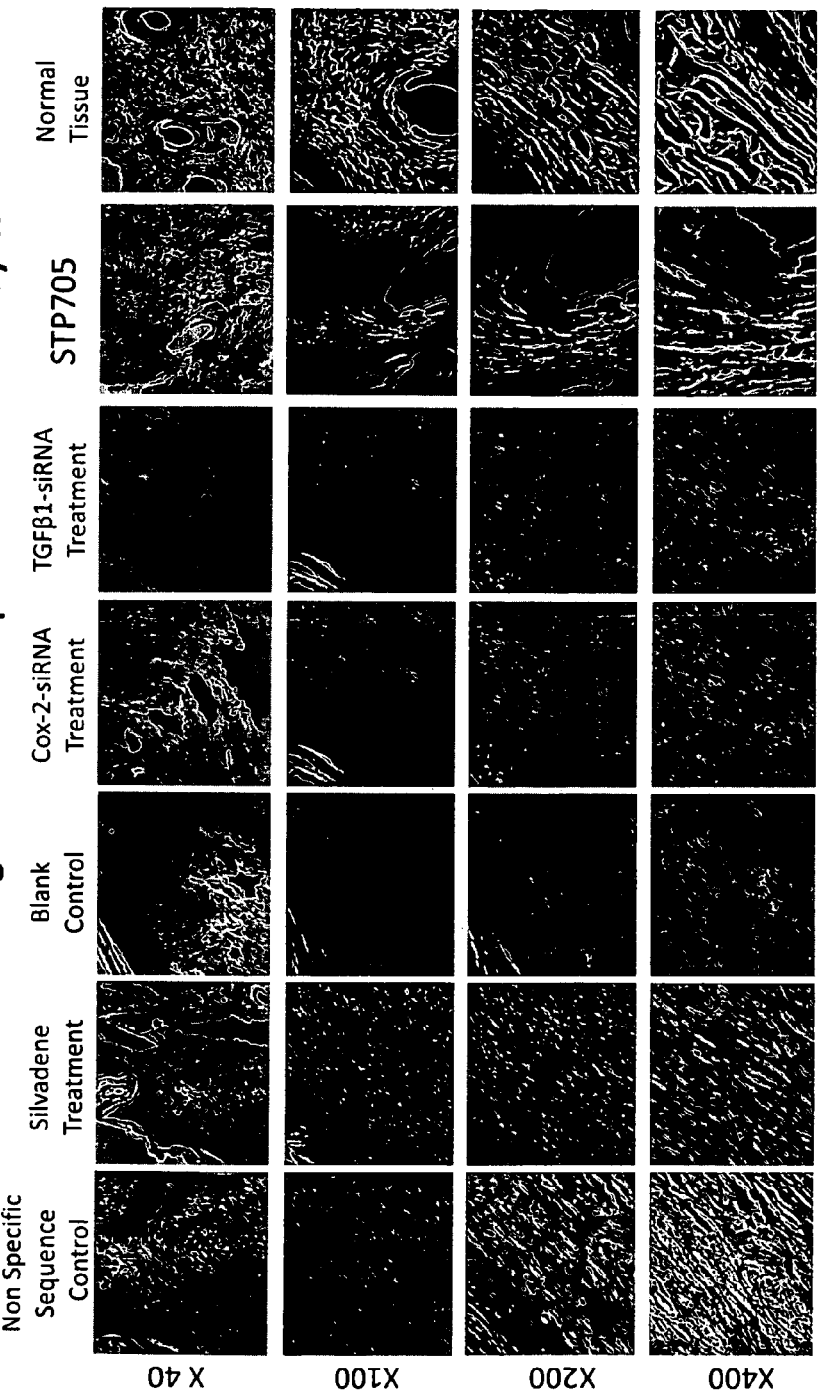
FIG. 13. STP705 Results in Normal Skin Structure. The tissue samples from the wound site of the pig skin on Day 47 were collected and subjected to Trichrome Staining As indicated in the figure, the STP705 treated tissue resulted in normal tissue like structure at four different magnifications.

Therefore, we further confirmed that STP705 is very effective for skin scarless wound healing on the pig excision wound model (FIG. 13).

Example 14

A Pig Skin Burn Wound was Used for Evaluation of STP705

A domestic female piglet (Taihuzhu, 15 kg) was anaesthetized with pentobarbital sodium at 40 mg/kg through ear vein injection, and a respirator was applied for breath assistance. The piglet was put on operation desk in supine position, and the back hair was shaved after sanitization. Full thickness skin wounds were established with an electric burning scalper. Experimental agents (STP705) were then applied to the wounds sites daily for total of 9 days with controls. Pictures were taken twice weekly to track changes. Biopsy samples were taken for pathology and IHC studies 91 days after the initial wounding. A machine was used to create homogeneous skin burn wounds (YLS-5Q, Shandong, China). The settings are 1.5 kg for pressure, 90° C. for temperature, and for 30 seconds. All wounds are 2 cm$^2$ in size. Eschars were shaved within 0.5-1.0 hour post burning for group one, and a 72 hours for group 2.

Example 15

STP705 is Effective on Pig Skin Burn Wound Model

Figure 14:
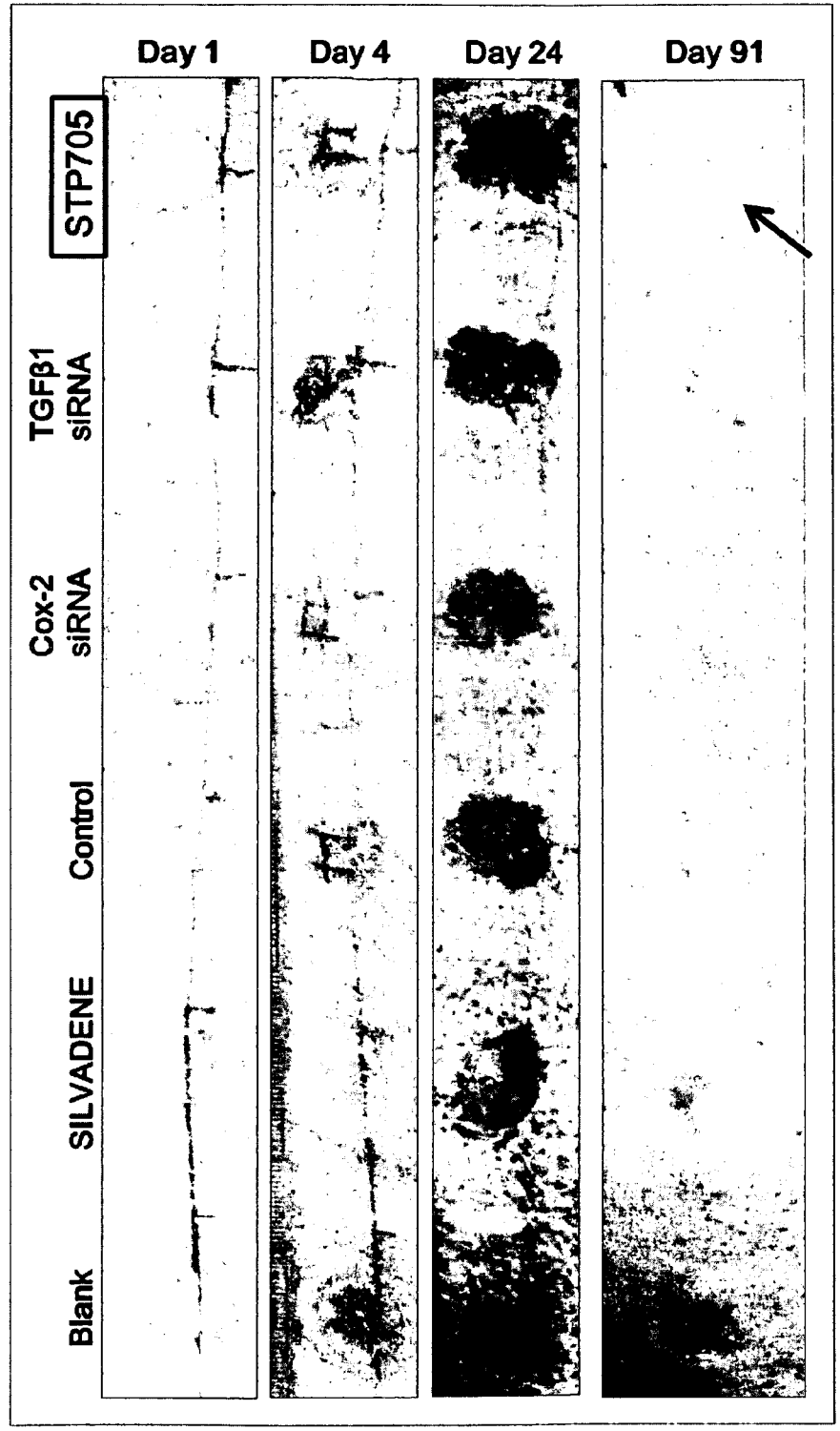
FIG. 14. STP705 Minimize Scar Formation in Pig Skin Burn Model. The pig skin burn model was established and applied for evaluation of STP705-mediated therapeutic effect. The pig skin burn wounds were treated with six groups: non-related siRNA sequence control, Silverdene, carrier only, Cox-2 siRNA only, TGF β1 siRNA only and STP705. The images were taken for every three days after the treatments. On day 91, STP705 treated wound exhibited very minimum scar pointed by arrow.
Figure 15:
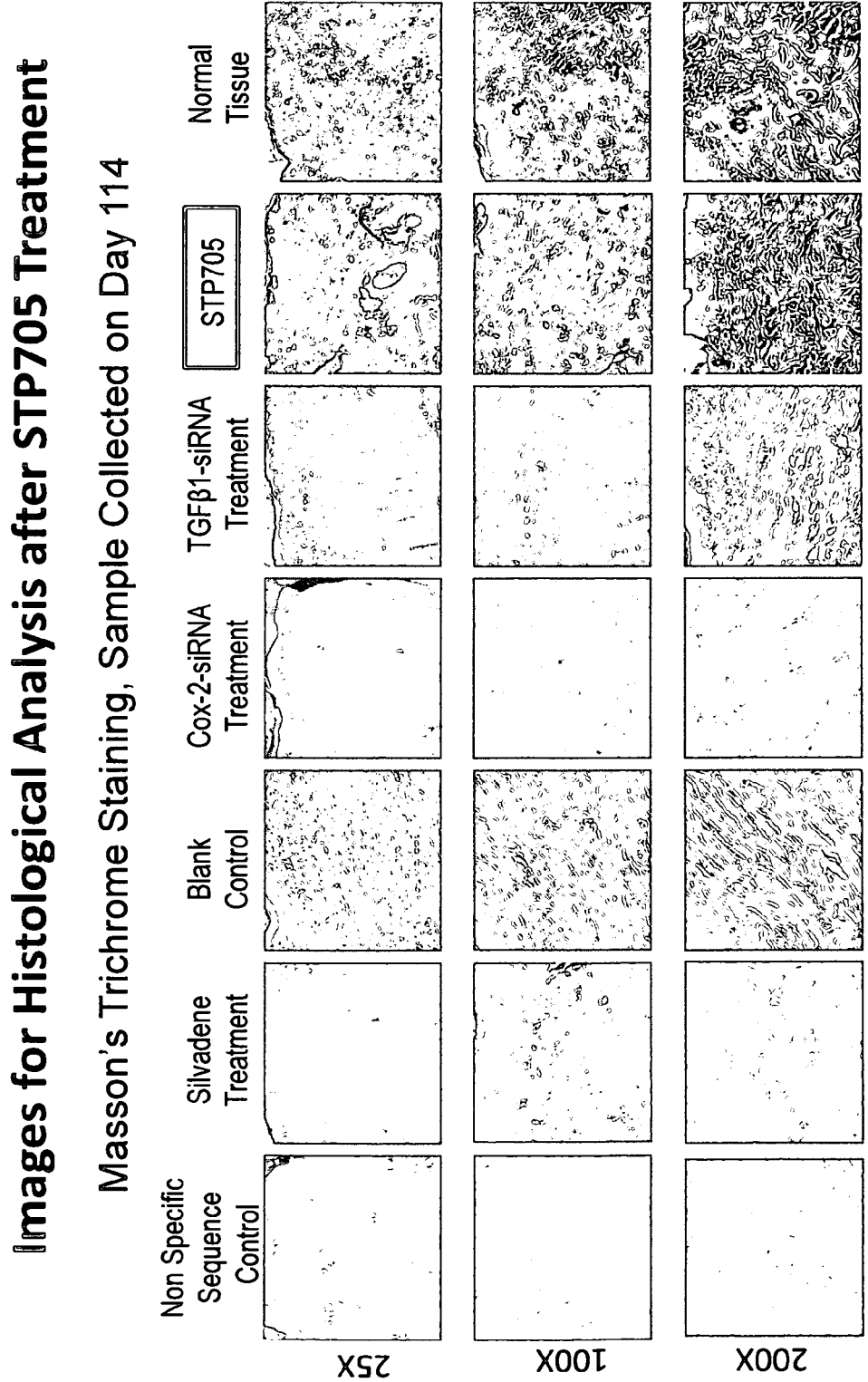
FIG. 15. STP705 Results in Normal Skin Structure in Pig Skin Burn Model. The tissue samples from the wound site of the pig skin on Day 114 after the treatment were collected and subjected to Trichrome Staining As indicated, the STP705 treated tissue exhibited a normal tissue like structure at three different magnifications.

The pig skin burn wound models have been widely accepted as the appropriated in vivo system for evaluation of skin scarless wound healing of human skin, after being burned by high temperature air, liquids and subjects, or by chemicals such as acitic or cationic liquid, due to their similar physiological and histological properties. The potent siRNA duplexes targeting either TGFβ1 or Cox-2 and with homology to both human and mouse are also homologous to the same genes in pig. Therefore, the same HKP Nanoparticle/siRNA formulation was tested on a pig skin excision wound model. A 30 pounds pig was used for the study. Wounds were established (2 cm) with a machine (YLS-5Q, Shandong, China) and then treated using the methylcellulose-HKP-siRNA nanoparticles cream and controls: (1) non-related siRNA; (2) positive control drugs used in the local hospital; (3) no treatment; (4) TGFβ1-siRNA; (5) Cox-2-siRNA and (6) combination of TGFβ1 and Cox-2 siRNAs. The wounds were topical treated daily with a dosage of 17 μg/200 μl/day, for 9 days and the animal behavior and wound appearances were observed daily. This animal study was carried out with the standard protocols approved. by the IACUC committee of Suzhou University (FIG. 14). The animal wounds were examined daily and the images on day 1, 4, 24 and 91 are illustrated. The histology analyses (day 92) showed clearly normalized tissue structure in the STP705 treated wound comparing the partial normalized and scaring tissues of other wounds with or without treatments (FIG. 15).

Example 16

Histological Analysis for Anti-Scar Effect of STP705 on Pig Skin Burn Wound

The tissue samples were collected from each wound site for histological analyses of the therapeutic benefit of STP705 on the pig skin burned wound model. The Trichrome staining was used. In addition to the samples from the following groups: (1) non-related siRNA; (2) positive control drugs used in the local hospital; (3) no treatment; (4) TGFβ1-siRNA; (5) Cox-2-siRNA and (6) combination of TGFβ1 and Cox-2 siRNAs, the normal tissue also was used to compare the treatment results. With 3 different magnifications, ×25, ×100 and ×200, the comparisons were made to observe the differences among groups. Clearly the textures of STP705 treated tissue samples are very much like the normal tissue's texture, verses the scar tissue like textures from other control groups. Therefore, we further confirmed that STP705 is very effective for skin scarless wound healing on the pig skin burn wound model (FIG. 15).

Example 17

Combination of siRNA Duplexes to Enhance Bigger Skin Wound Closure

Figure 16:
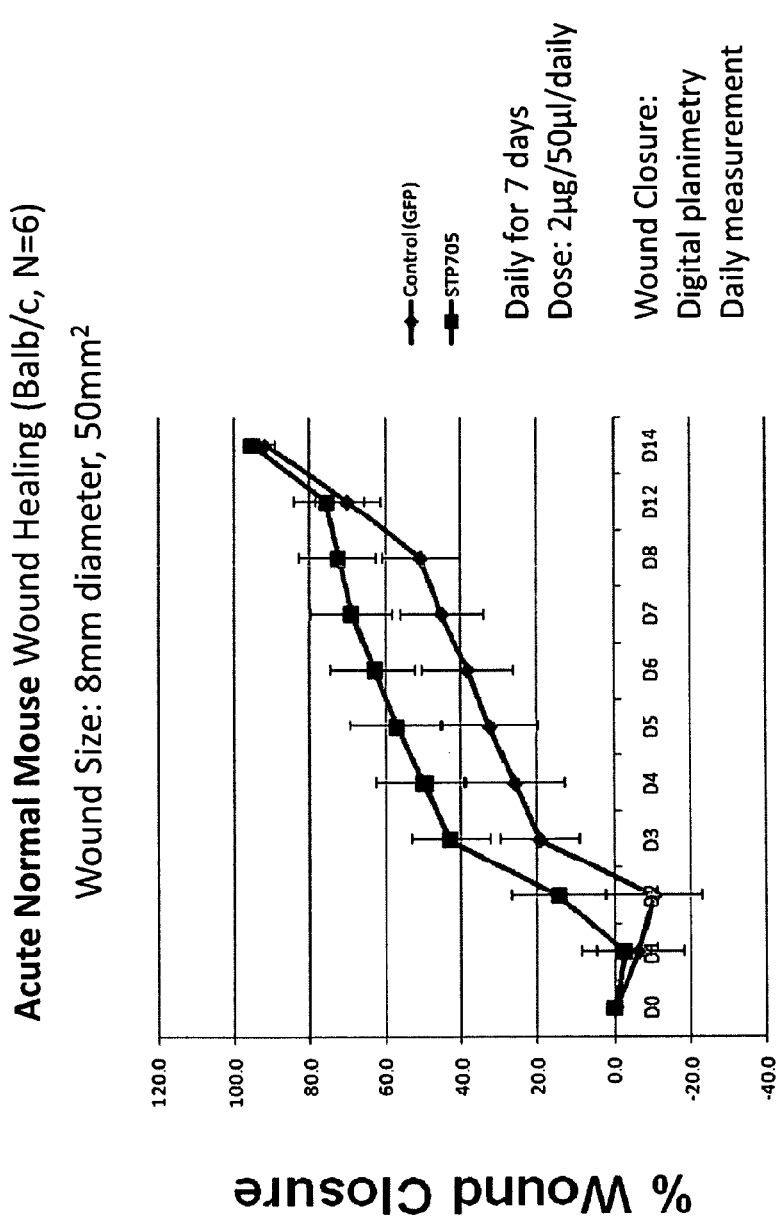
FIG. 16. STP705 Improved Wound Closure with Mouse Skin Excision Wound Model (bigger wound size). A bigger skin wound size (8 mm in diameter, 50 mm$^2$) was used for evaluation of STP705. The STP705 treated wounds (cohort size N=6) showed faster wound closure measured and quantified with a Digital planimetry.

In order to evaluate the synergistic effect of combining potent siRNA duplexes targeting both TGFβ1 and Cox-2 with a bigger mouse excision wound, we tested STP705 in HKP nanoparticle with the 8 mm skin excision wound on mouse back. The target gene knockdown and wound closure (FIG. 16) were evaluated. The control siRNA sequence is a GFP (green fluorescence protein) specific sequence without homology to either TGFβ1 or Cox-2 gene. Daily administration for 7 days with dose: 2 µg/50 µl. The TGFβ1-Cox-2 siRNA pair demonstrated evident benefit for wound closure started at day 2 and all the way to day 8 (cohort size N=6). The wound closure speed was measured daily with a digital planimetry instrument.

Example 18

Figure 17:
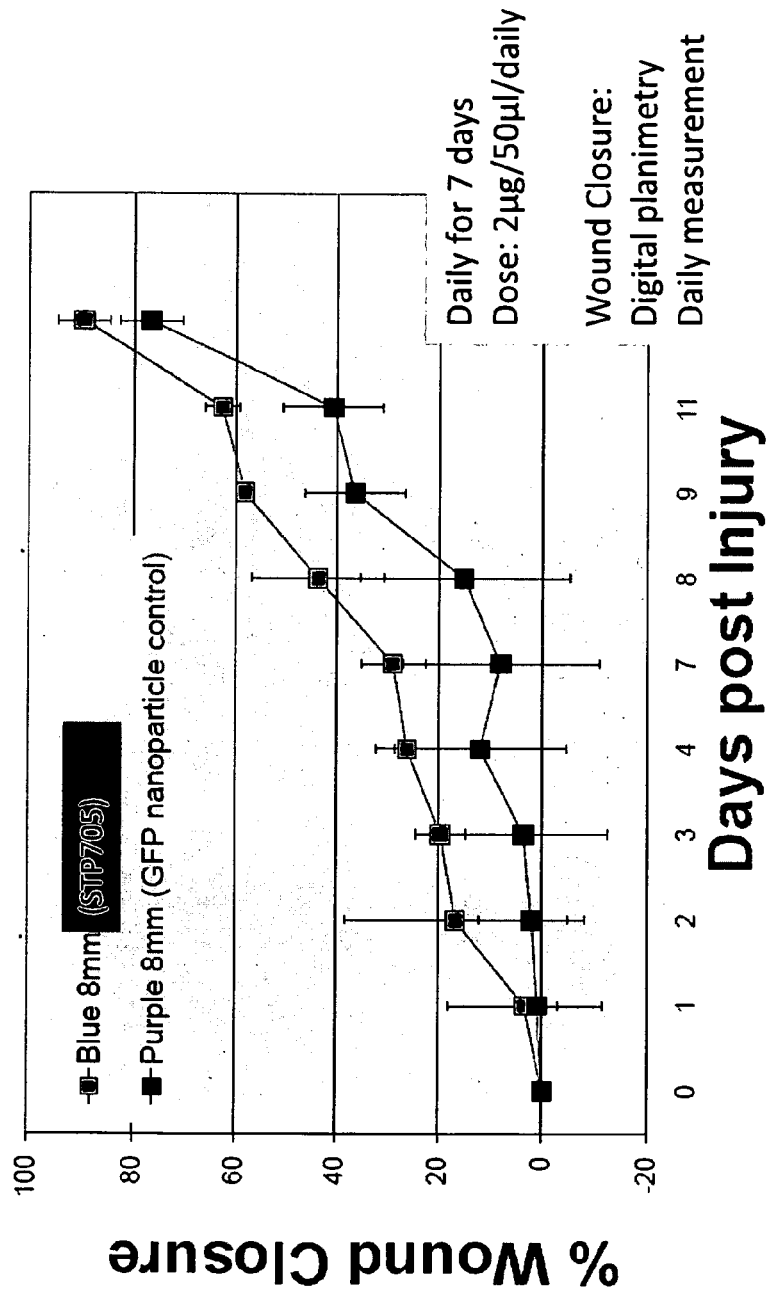
FIG. 17. STP705 Improved Wound Closure with Diabetic Mouse Model. A bigger skin wound size (8 mm in diameter, 50 mm$^2$) was used for evaluation of STP705 using a transgenic diabetic mouse (db+/db+). The STP705 treated wounds (cohort size N=5) showed faster wound closure measured and quantified with a Digital planimetry.

Combination of siRNA Duplexes to Enhance Skin Wound Closure with a Mouse Diabetic Model In order to evaluate the therapeutic benefit of STP705 using a transgenic mouse model (db$^+$/db$^+$, cohort size N=5), we tested STP705 with skin excision wound (8 mm in diameter) on mouse back. will have better results in wound closure and skin wound histopathological response. The target gene knockdown and wound closure were evaluated. The control siRNA sequence is a GFP (green fluorescence protein) specific sequence without homology to either TGFβ1 or Cox-2 gene. Daily administration for 7 days with dose: 2 µg/50 µl. The TGFβ1/Cox-2 siRNA pair demonstrated evident benefit for wound closure started at day 2 and all the way to day 11 (FIG. 17). The wound closure speed was measured daily with a digital planimetry instrument.

Example 19

Measurement for STP705-Mediated Gene Knockdown In Vitro

Figure 18:
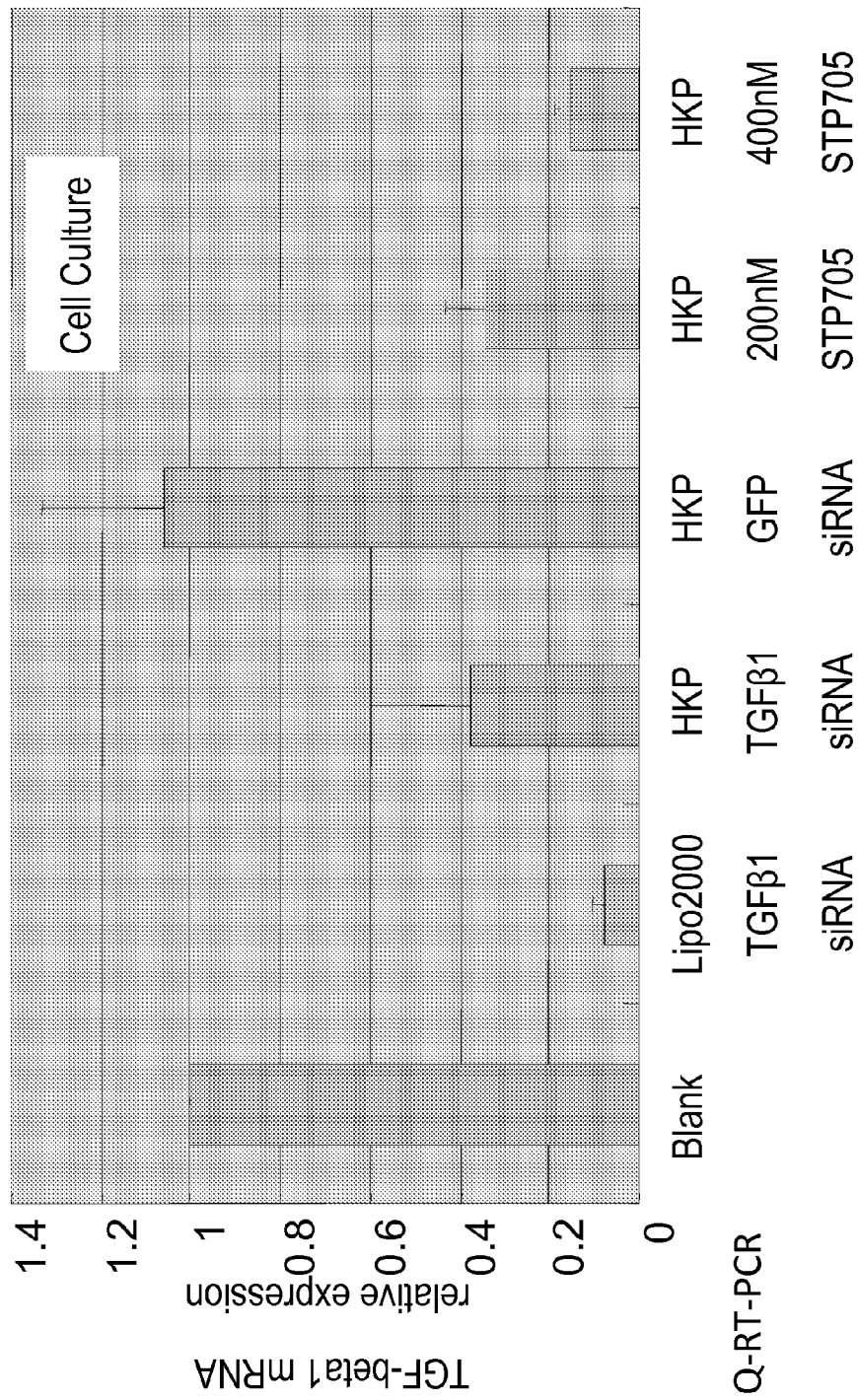
FIG. 18. Validation of STP705 for Target Gene Knockdown in Vitro. Using Hela cell culture, STP705 siRNA duplexes targeting both TGFβ1 and Cox-2 were transfected followed by total RNA isolation (48 hours) and Q-RT-PCR analysis. STP705 was able to knockdown TGFβ1 expression equivalent to TGFβ1-siRNA only packaged with HKP.

To demonstrate the target genes (TGFβ1 and Cox-2) knockdown with STP705 in vitro, we developed a cell culture transfection assay followed by Q-RT-PCR for quantitative measurement. First we make methylcellulose as concentrated as possible with distilled water, then dilute with 4×DMEM medium to 1% final concentration. STP705 was formulated according to the method of wound healing for pigs an mice. Growing Hela cells to 70-80% confluence, and then add STP705 onto cultures. Changing media by adding 1 ml DMEM medium containing 10% FBS after incubating 4 hours. Twenty 20 hours later, the total RNA was extracted for Q-RT-PCR detection of TGFβ1 mRNA expression. As indicated in FIG. 18, six groups with different treatments were used as following: (1) untreated; (2) Positive Control with Lipofectamine 2000 (or HKP) and TGFβ1-siRNA at 50 nM; (3) Positive Control with Lipofectamine 2000 (or HKP) and TGFβ1-siRNA at 100 nM; (3) Negative Control with HKP-GFP-siRNA at 200 nM in 1.5% methycellulose; (4) Test with HKP-(C+T)-siRNA at 200 nM in 1.5% methycellulose; (5) Test with HKP-(C+T)-siRNA at 400 nM in methyethycelluloase. From the result, comparing with the blank or Negative Control group, it is observed that the mRNA expression of TGFβ1 was reduced by 30% and 50% after the treatment with 200 nM of STP705 and 400 nM of STP705 respectively.

Example 20

Measurement for STP705-Mediated Gene Knockdown in Cultured Skin Tissue

Figure 19:
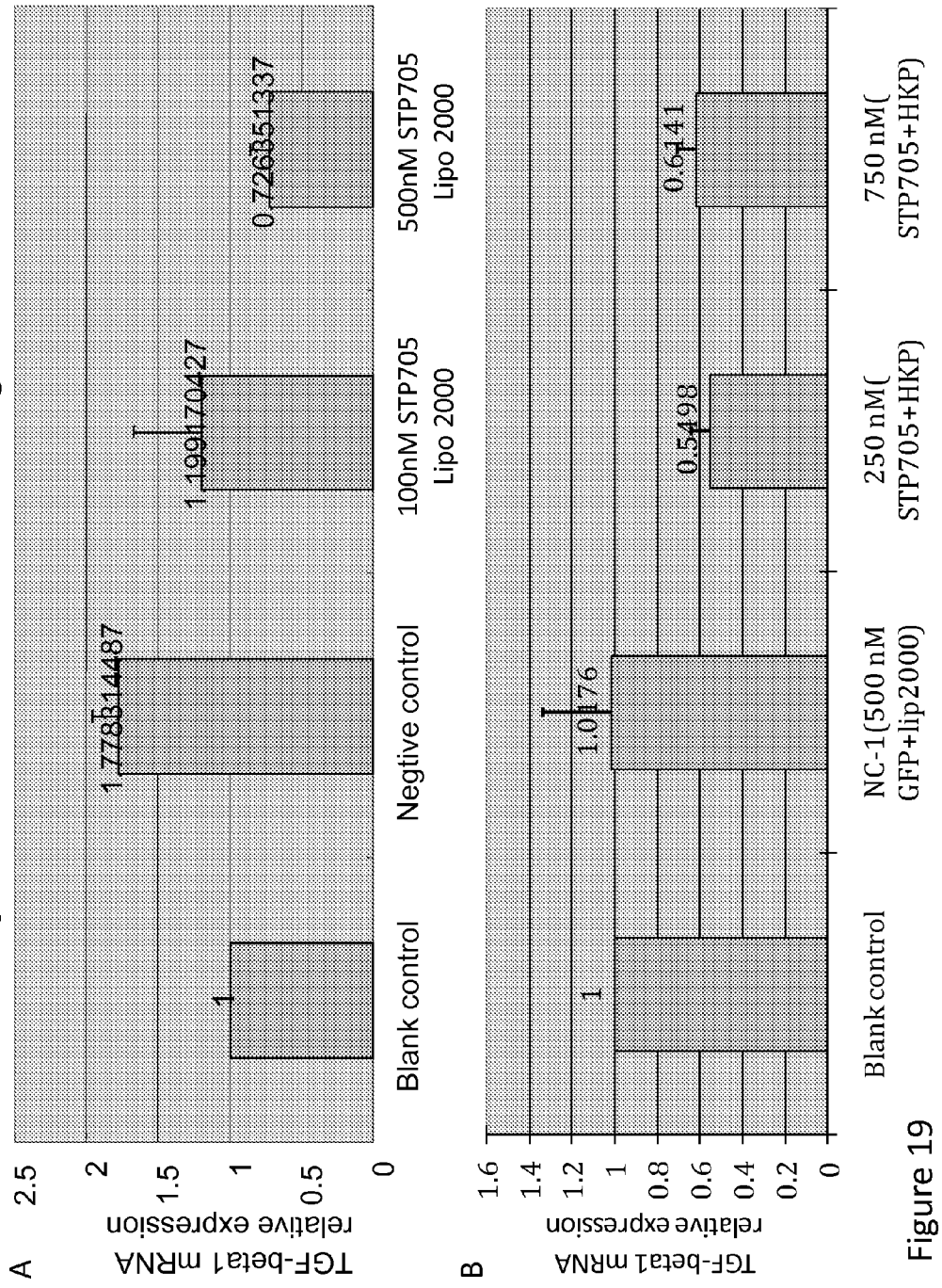
FIG. 19. STP705-Mediated TGFβ1 Gene Knockdown in Organ Culture. The transfection of mouse skin was carried out with the TGFβ1 and Cox-2 siRNAs packed by the lipfectamine 2000 (A) or STP705, followed by total RNA isolation and Q-RT-PCR. Each treatment includes the Normal Control as the base level, the β-actin as the housekeeping gene. Two different dosages of STP705 were used and both of them illustrated significant TGFβ1 knockdown.
Figure 20:
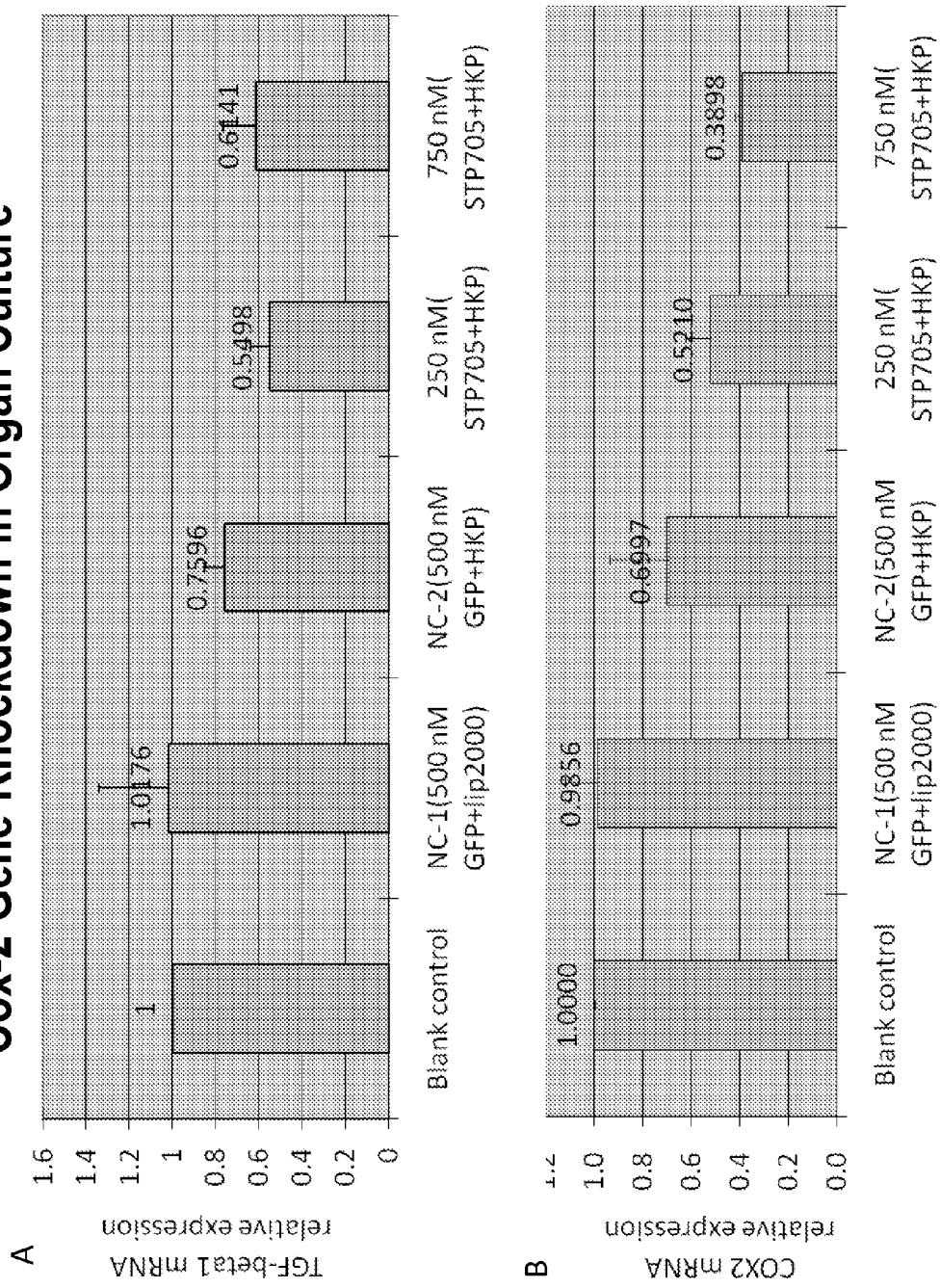
FIG. 20. STP705-Mediated Cox-2 Gene Knockdown in Organ Culture. The transfection of mouse skin was carried out with the TGFβ1 and Cox-2 siRNAs packed by the lipfectamine 2000 (A) or STP705, followed by total RNA isolation and Q-RT-PCR. Each treatment includes the Normal Control as the base level, the β-actin as the housekeeping gene. Two different dosages of STP705 were used and both of them illustrated significant Cox-2 knockdown.

To evaluate efficiency of STP705-mediated knockdown of the target genes (TGFβ1 and Cox-2) in a model system which is more relevant to the animal skin tissues, we established an ex vivo approach using the in vitro organ tissue culture followed by Q-RT-PCR or immunohistochemistry assays. The transfection of mouse skin tissues were conducted using siRNA duplexes (targeting TGFβ1 and Cox-2) packed by the lipfectamine 2000 or by Histidine-Lysine polymer (STP705 formulation) in vitro. FIG. 19 has demonstrated TGFβ1 gene knockdown with Lipo2000-mediated TGFβ1/Cox-2 siRNA transfection in the organ culture (A) and STP705-mediated TGFβ1 gene knockdown in the organ culture (B). Clearly, both transfection approaches were able to achieve significant gene silencing of TGFβ1 in the organ culture. FIG. 20 has demonstrated Cox-2 gene knockdown with Lipo2000 mediated TGFβ1/Cox-2 siRNA transfection in the organ culture (A) and STP705-mediated Cox-2 gene knockdown in the organ culture (B). Clearly, both transfection approaches were able to achieve significant gene silencing of Cox-2 gene in the organ culture.

Example 21

Measurement for STP705-Mediated Gene Knockdown In Situ

Since the organ culture assay was used for evaluation of target gene silencing in the skin tissue, we also developed immunohistochemistry assay to measure the protein expression levels of both TGFβ1 and Cox-2. The experimental details are described as following: paraffin embedded sections were deparaffinised in xylene and rehydrated through a graded series from ethanol to water. The antigen retrieval was performed by heating slides immersed in EDTA-Tris solution (10 mM Tris, 1 mM EDTA, pH9) using microwave oven for 15 min at low temperature. After washing sections with PBS. Endogenous peroxidase activity was blocked by incubation in 3% hydrogen peroxide for 10 min. and 5% bovine serum albumin (BSA) for 20 min. The sections were incubated overnight at 4° C. with the rabbit polyclonal antibodies (anti-cox2), and using the PBS as the negative control. Washing sections with PBS. The sections were incubated with the biotinylated goat anti-rabbit antibody for 20 min at room temperature. Washing sections with PBS.

Figure 21:
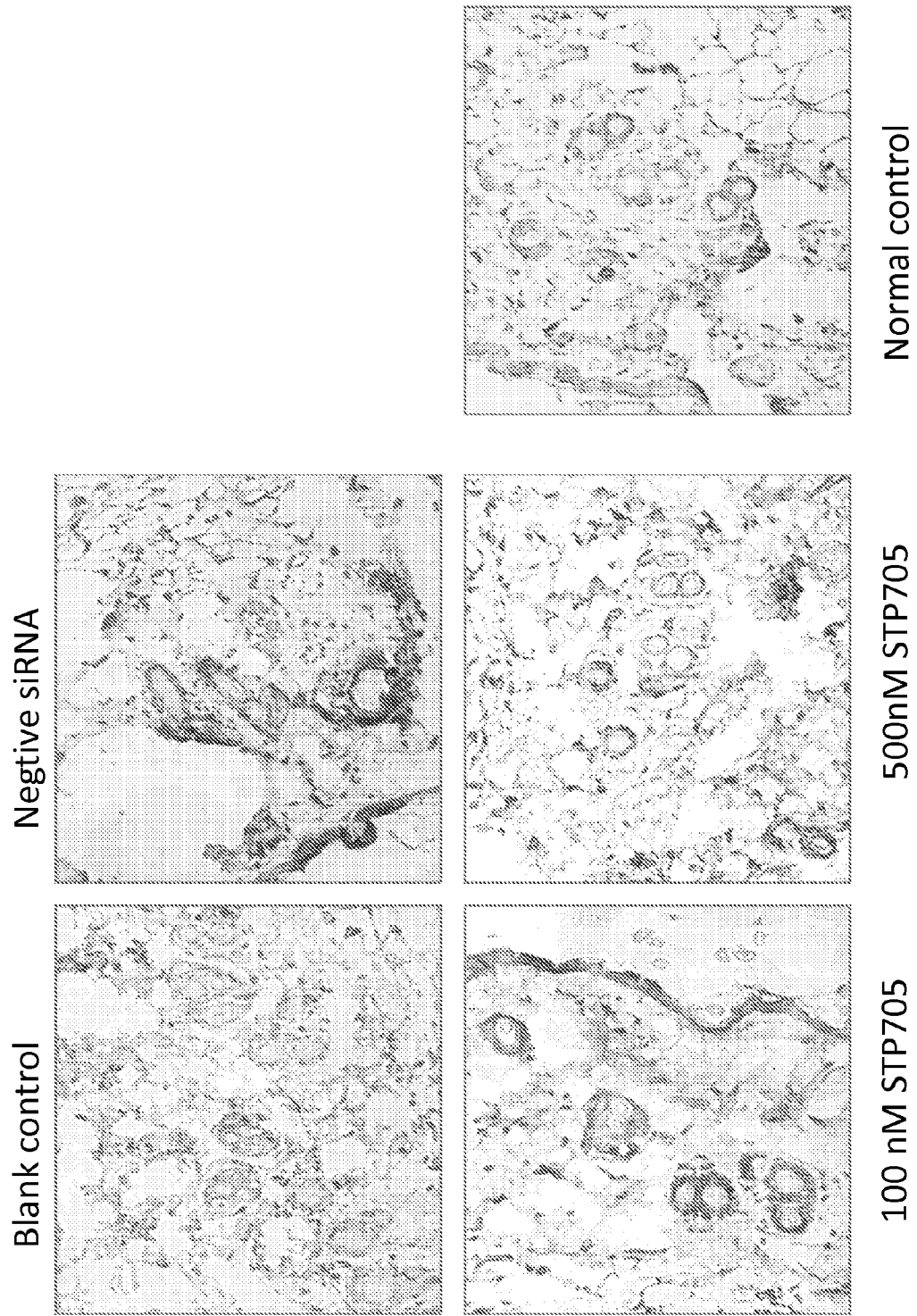
FIG. 21. STP705-Mediated TGFβ1 Gene Knockdown in Organ Culture. The transfection of mouse skin was carried out with the TGFβ1 and Cox-2 siRNAs packed by the lipfectamine 2000 (A) or STP705, followed by immunohistochemistry of TGFβ1 protein expression in the mouse skin samples as the organ culture. The TGFβ1 staining (400×) Illustrations: The tissues of normal control group were not cultured in vitro before fixed in the formalin. On the contrary, the skins of other groups were all cultured 24 hrs before fixed, and the transfection were done with the lip2000 during this time of 24 hrs, and using the 500 nM GFP siRNA as the negative control group.
Figure 22:
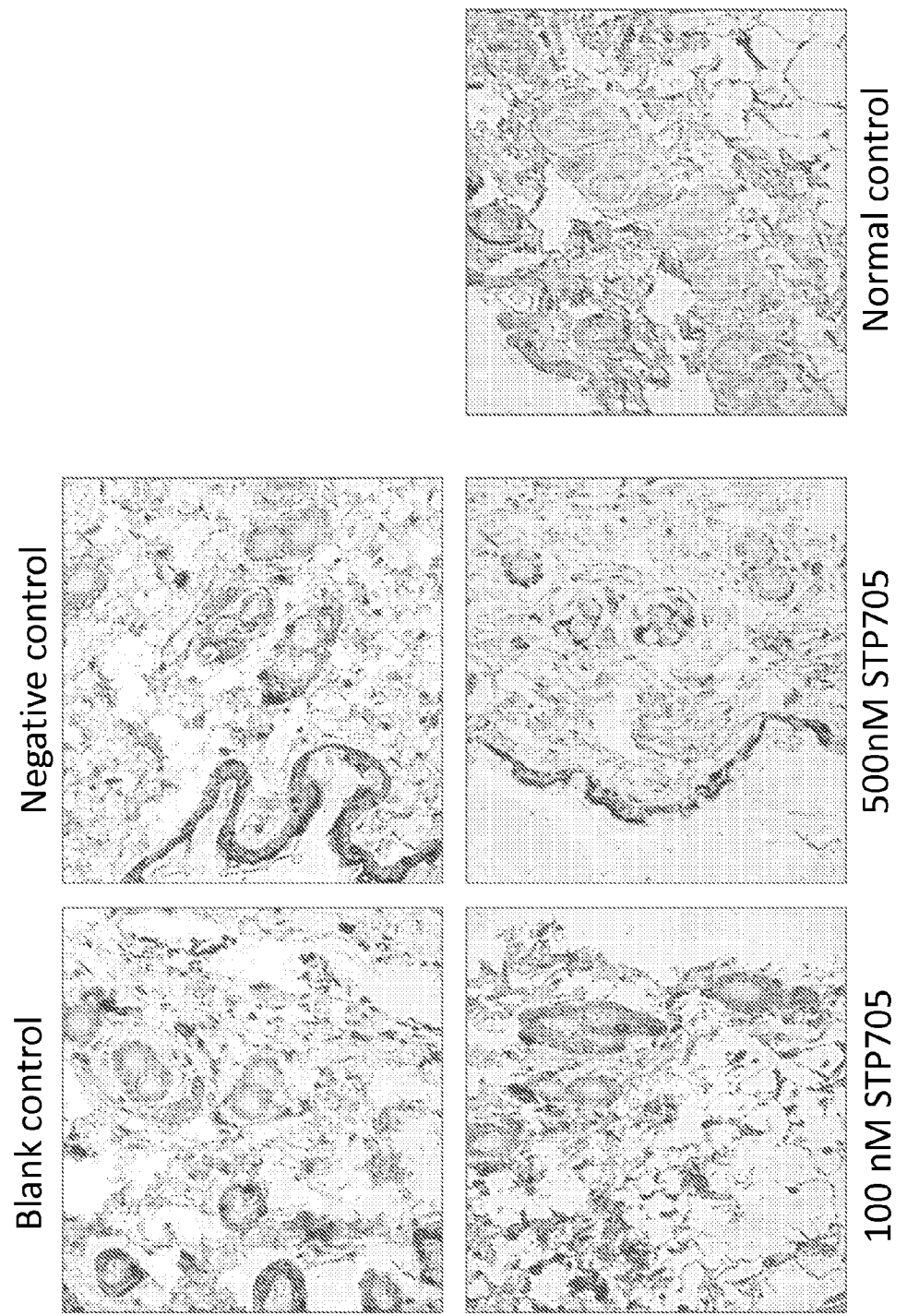
FIG. 22. STP705-Mediated Cox-2 Gene Knockdown in Organ Culture. The transfection of mouse skin was carried out with the TGFβ1 and Cox-2 siRNAs packed by the lipfectamine 2000 (A) or STP705, followed by immunohistochemistry of TGFβ1 protein expression in the mouse skin samples as the organ culture. The Cox-2 staining (400×) Illustrations: The tissues of normal control group were not cultured in vitro before fixed in the formalin. On the contrary, the skins of other groups were all cultured 24 hrs before fixed, and the transfection were done with the lip2000 during this time of 24 hrs, and using the 500 nM GFP siRNA as the negative control group.

The sections were incubated with the agent SABC of the kit for another 20 min at room temperature. Washing sections with PBS. The freshly prepared 3,3-diaminobenzidine tetrahydrochloride was used to visualize antibody binding. Sections were counterstained with hematoxylin; Dehydration; Clearing and overslipping. The results are showed in FIG. 21 that the signals of TGFβ1 protein staining are significantly down regulated after the in vitro transfection of STP705 to the organ culture. FIG. 22 also exhibits that the signals of Cox-2 protein staining are significantly down regulated after the in vitro transfection of STP705 to the organ culture.

Example 22

Combinational Benefit of TGFβ1/Cox-2 SiRNAs on Scarless Wound Healing

Wound healing, whether initiated by trauma, microbes or foreign materials, proceeds via an overlapping pattern of events including coagulation, inflammation, epithelialization, formation of granulation tissue, matrix and tissue remodeling. The process of repair is mediated in large part by interacting molecular signals, primarily cytokines, that motivate and orchestrate the manifold cellular activities which underscore inflammation and healing. Skin wound healing is a complicated process, which has been considered to occur in three stages: inflammatory stage, proliferative stage and remodeling stage. There are abundant studies demonstrating that latent TGFβ1, released in large quantities by degranulating platelets, is activated from its latent complex by proteolytic and non-proteolytic mechanisms to influence wound healing from the initial insult and clot formation to the final phase of matrix deposition and remodeling. Active TGFβ1 elicits the rapid chemotaxis of neutrophils and monocytes to the wound site[5] in a dose-dependent manner through cell surface TGFβ serine/threonine type I and II receptors and engagement of a Smad3-dependent signal. TGFβ1. Of the myriad of cytokines that have been investigated in terms of wound healing, TGFβ1 has undoubtedly the broadest effects. The observations have broad implications for understanding the role of TGFβ1 in the endogenous wound healing response, in that an excess of TGFβ1 may be a normal constituent of the response for rapid and optimal protection of the host. In the absence of infection, however, reduction of this overexuberant recruitment, inflammation and keratinocyte suppression may result in a more cosmetically acceptable scar. This knowledge may allow us to optimize the response by modulating selective cell pathways and to tailor therapy to specific cellular defects in pathological conditions such as chronic ulcers and fibrotic processes. On the other hand, metabolites and enzymes of the arachidonic acid cascade, including the cyclooxygenase-2 (COX-2) enzyme and its enzymatic product prostaglandin E2 (PGE2), are known to be critical mediators of the inflammatory response. COX-2 has received much attention recently as it is involved in diseases associated with dysregulated inflammatory conditions, such as rheumatoid and osteoarthritis, cardiovascular disease, and the carcinogenesis process. COX-2 undergoes immediate-early up-regulation in response to an inflammatory stimulus, such as a wound. It functions by producing prostaglandins that control many aspects of the resulting inflammation, including the induction of vascular permeability and the infiltration and activation of inflammatory cells. Interest in the role of the COX-2 pathway and other aspects of inflammation in the adult wound repair process is increasing as these early events have been shown to regulate the outcome of repair. Based on the involvement of COX-2 in the inflammation, it has been suggested that the COX-2 pathway is involved in scar production in fetal skin and that targeting COX-2 may be useful for limiting scar formation in adult skin.

Figure 23:
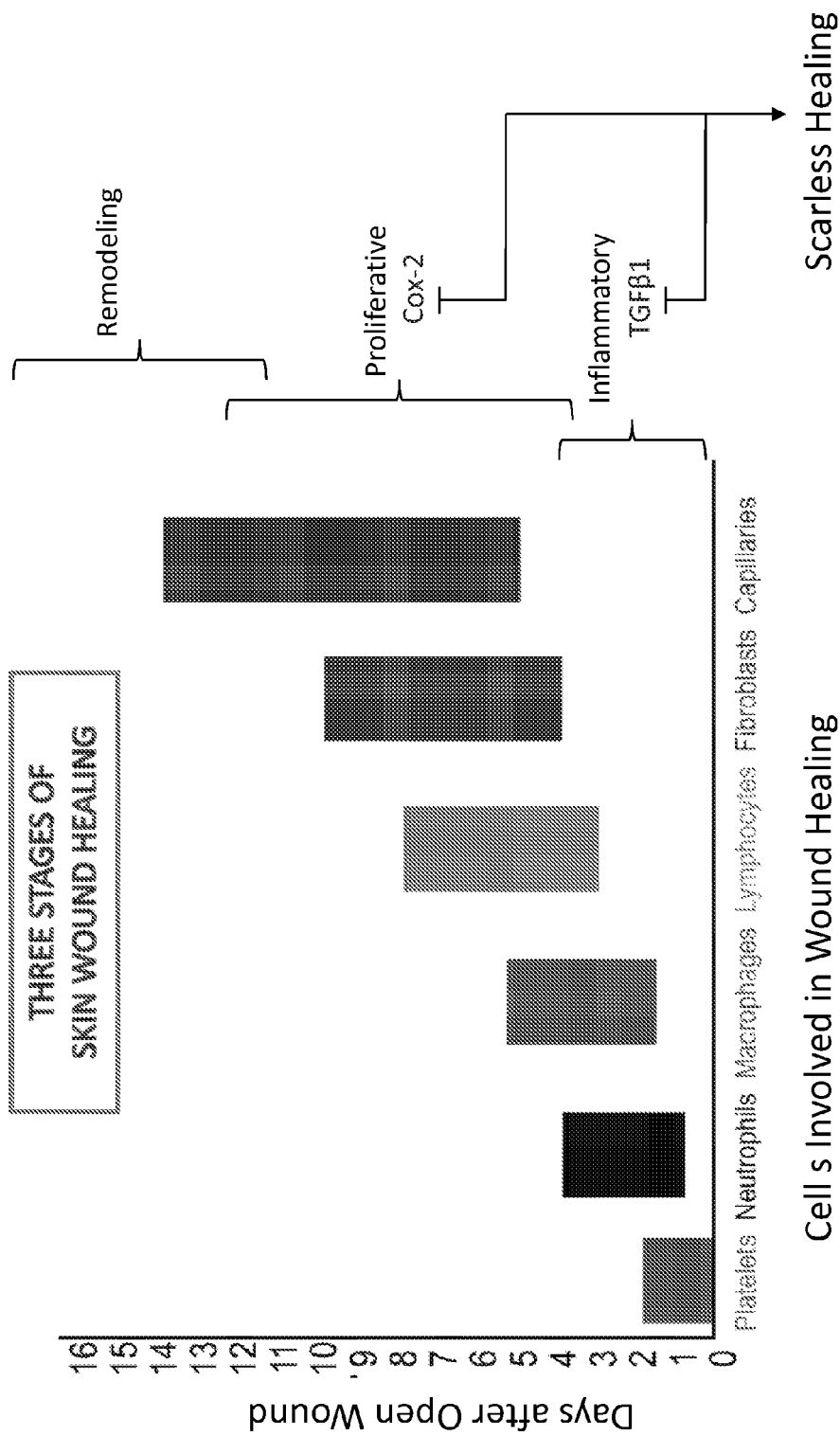
FIG. 23. Hypothesis and Mechanism of Actions. Skin wound healing is a complicated process involving in many physiological pathways and multiple cell types as shown in the figure. TGFβ1 is an important pro-inflammatory factor responsible for the early response to the open wounds recruiting platelet, neutrophils and microphages. Overexpression of TGFβ1 will induce server inflammation on the wound site which will affect the later proliferation and remodeling stages resulting scar formation. Using siRNA to silence TGFβ1 expression on the wound site will reset the balance of the cytokine expression profile resulting in better wound healing and less scar formation. Cox-2 is heavily involved in the fibroblast proliferation which is the key factor for scar formation. The combination of the inhibitors to TGFβ1 and Cox-2 further enhanced the regulation of the factors involved in the wound healing process. We believe that the resulting accelerated wound closure and less scar formation is due to the utilization of siRNA cocktail targeting both factors in the same regimen.

The combination of siRNA inhibitors targeting both TGFβ1 and Cox-2 may provide the unique therapeutic benefit through down-regulation of multiple inflammatory factors and reestablishing the balance between re-epithelialization and scarring. Silencing TGFβ1 may mostly involve in the inflammatory stage of the wound healing by tuning down the expressions of cytokines and chemokines which are not required for the wound healing process in a clean environment such as surgery room. Silencing Cox-2 may have stronger effects on the proliferative stage by minimizing the proliferation of fibroblasts (FIG. 23). The combined effect could minimize scar formation during the skin wound repairing process while preserving the physical strength of the healed skin.

Example 23

Combinations of TGFβ1/Cox-2 siRNA for Other Therapeutic Application

Figure 24:
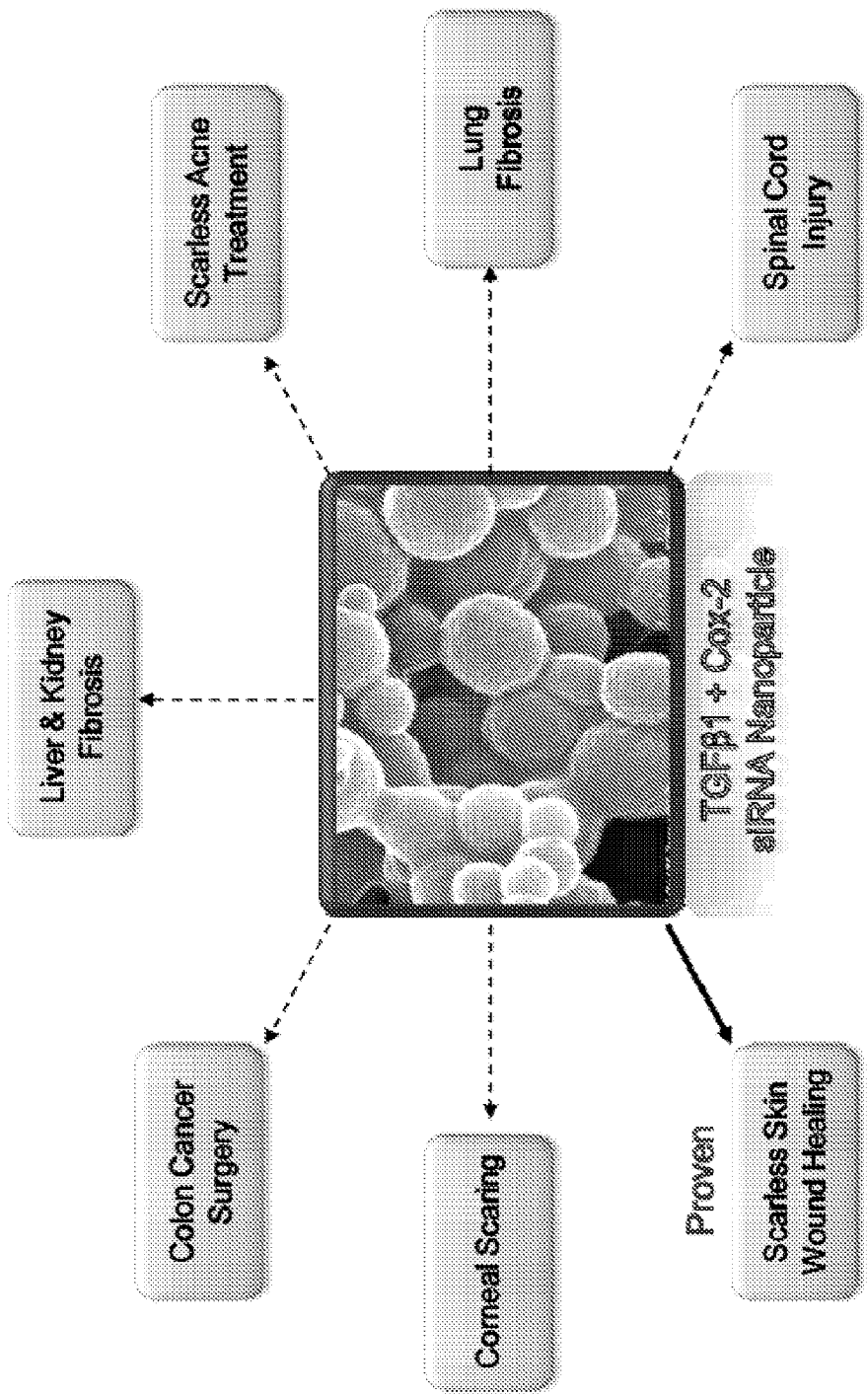
FIG. 24. We have demonstrated the effect of siRNA therapeutics targeting both TGFβ1 and Cox-2 in the skin excision wound model. We believe that this inhibitor combination can be widely applied to treat many other pathological processes involved in the scar formation and fibrosis. Those disease conditions include corneal and retina scaring, internal tissue scaring due to the injury or surgery, lung fibrosis, liver fibrosis and kidney fibrosis, tendon scaring, spinal cord injury, muscle scaring and acne scaring, etc. This inhibitor combination can also be used for certain types of cancer treatment.

Response to injury is frequently modeled in the skin, but parallel coordinated and temporally regulated patterns of mediators and cellular events occur in most tissues subsequent to injury. The initial injury triggers coagulation and an acute local inflammatory response followed by mesenchymal cell recruitment, proliferation and matrix synthesis. Failure to resolve the inflammation can lead to chronic nonhealing wounds, whereas uncontrolled matrix accumulation, often involving aberrant cytokine pathways, leads to excess scarring and fibrotic sequelae. Continuing progress in deciphering the essential and complex role of cytokines in wound healing provides opportunities to explore pathways to inhibit/enhance appropriate cytokines to control or modulate pathologic healing. Learned from the skin wound healing process and evaluated the possibility of using such TGFβ1/Cox-2 siRNAs packaged in the HKP, we believe that this novel compound will be applicable for other types of therapeutic application. The rational is that the mechanism of the scar formation in other tissues rather than skin is very similar. The scaring itself caused major medical problems: e.g. the scarring can cause hazy vision or blindness; in the peripheral and central nervous system where scarring prevents neuronal reconnections and hence restoration of neuronal function; in the gastrointestinal and reproductive organs, where strictures and adhesions caused by scarring can give rise to serious or life-threatening conditions such as infertility or failure of bowel function; in ligaments and tendons where scarring where scaring restricts movement, decrease strength and prevents normal function, etc. TGFβ1/Cox-2 siRNAs packaged in the HKP or other delivery vehicles can be an alternative approach to treat the above conditions (FIG. 24).

Example 24

Combinations of TGFβ1/Cox-2 siRNA For Tissue Fibrosis Treatment

Fibrosis occurs in adult as a usual outcome of recovery to organ damage, which, although acts to stop bleeding and repair damages, will inevitably leads to many unwanted endings, including scaring of damaged organs. It is not hard to imagine that scarring will affect normal functions if it happens in mesenchymal organs like liver, lung and kidney. Therefore, our invention will have a huge impact to the quality of life of those patients. Scarring, or fibrogenesis after injuries is a complex process which involves many types of cells during several stages of recovery. Inflammation is an indispensible part of the wound healing process during which many inflammatory cells are interacting with each other. Cytokines no doubt play crucial roles for the whole process, especially at initial stages. TGFβ1 among all is the most important cytokine promoting the fibrosis of parenchymal organs after injury.

It is estimated that about 80% of all collagen-producing cells are from hepatic stellate cells in which response to injuries undergo EMT (epithelial mesenchymal transformation) from quiescent vitamin A containing mesenchymal cells to morphologically different and functionally active myofibroblasts. Irregular deposition of large amounts of collagens, especially type I collagen, leads to liver fibrosis (cirrhosis), loss of function and induction of hepatocellular carcinoma. Among all cytokines TGFβ1 is considered as the primary stimulator of HSC activation, and therefore the primary therapeutic target of drug development. The major sources of TGFβ1 in liver are resident macrophages, (Kupffer's cells) and bone marrow derived macrophages. These cells are activated by tissue injury and in turn cause tissue inflammation at damage spot. It is known that COX2 plays an important role in inflammations by promoting production of many inflammatory molecules such as prostaglandins, and leukotrienes indirectly, which are immediate mediators of inflammation, dilating small vessels, increasing blood exudation, recruiting leukocytes and macrophages, which are one of the major sources of TGFβ1. A hypothesis is proposed here that liver cirrhosis may be blocked if production of TGFβ1 can be down-regulated, and then fewer HSC will transform to myofibroblasts, which secrete mainly type I collagen, of which scar is made.

Lung Fibrosis: Deregulated EMT also appears to occur in some lung diseases, of which the pathogenesis shows chronic degenerative fibrosis of pulmonary tissue. Such disorders include Idiopathic Pulmonary Fibrosis (IPF), and lung scarring after recovering from acute or chronic insults like infections, or hemostasis. The pathogenesis of IPF is characterized by loss of lung alveolar epithelial cells (AECs) due to injuries, accumulation of fibroblasts/myofibroblasts and abnormal deposition of type I collagen in the lung parenchyma. The prognosis for IPF patients is poor and current therapies are largely ineffective in preventing respiratory failure. The primary effector cells in parenchyma fibrosis are myofibroblasts, which may be derived by the activation and proliferation of resident lung fibroblasts, from epithelial-mesenchymal transition (EMT), or through recruitment of circulating fibrocytes. Among many profibrotic cytokines TGFβ1 is nonetheless a central regulator of pulmonary inflammation and fibrosis. TGFβ1 induces EMT in alveolar epithelial cells (AECs) in vitro and in vivo. TGFβ1 not only increases fibroblast proliferation, and stimulates the synthesis and deposition of collagen, but also inhibits the collagen breakdown by collagenase. But the role of COX2 in IPF is uncertain at this moment. Some data even show that COX2 down-regulation would make fibrosis worse in a COX2 KO mouse model.

Figure 25:
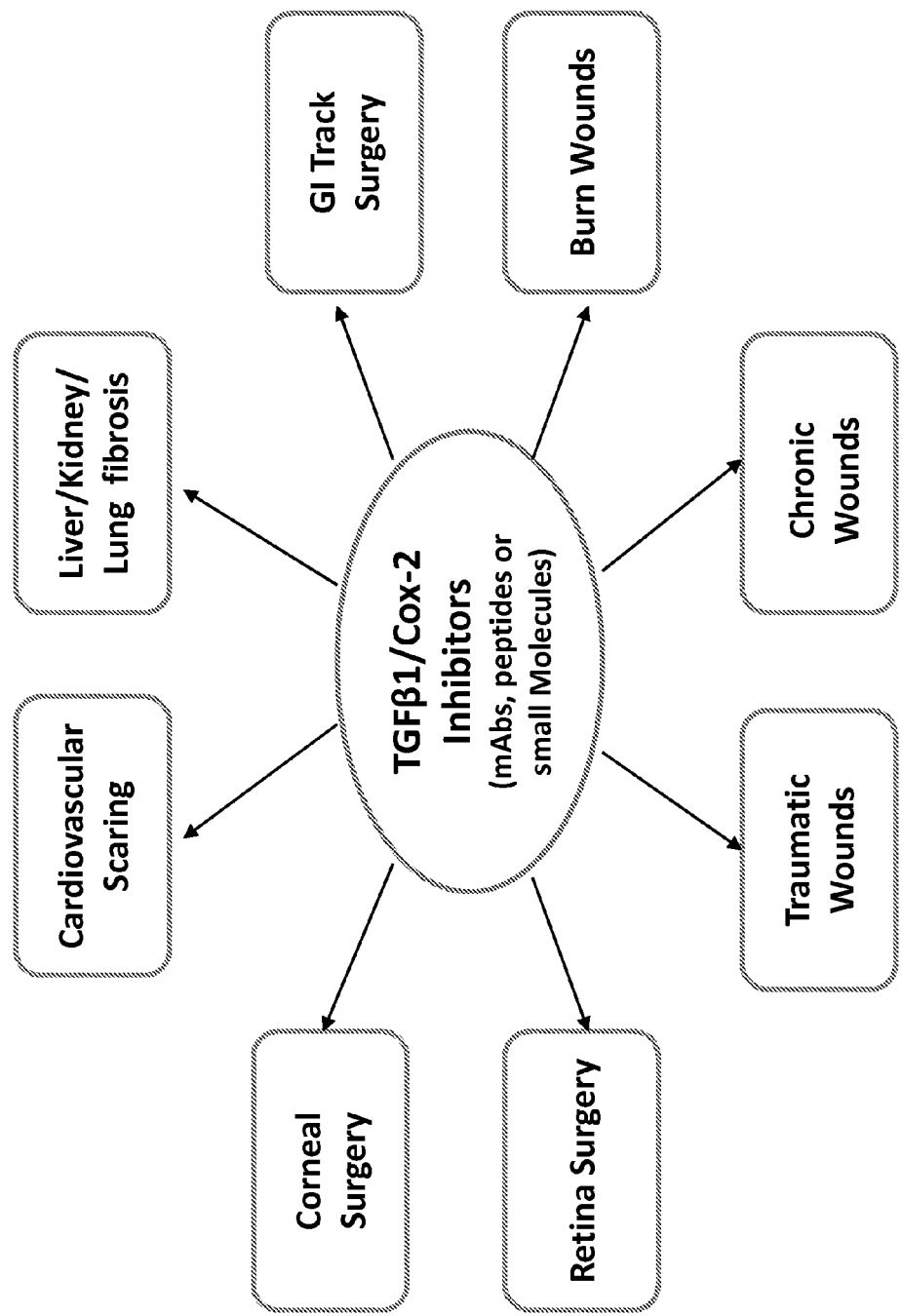
FIG. 25. Combination of TGFβ1 and Cox-2 Inhibitors will have Broad Applications. Since siRNA therapeutic is taking advantage of target gene silencing, we are hypothesizing that using the antagonist drugs against the same targets in combination will have the similar therapeutic benefit we discovered in our study: the combinations of small molecule drugs, monoclonal antibody drugs and other inhibitory modalities will have the synergistic therapeutic benefits as we observed with STP705.

Kidney Fibrosis: Fibrosis is a characteristic phenomenon of recovery for various kidney diseases due to insults ranging from immunological, hypertensive, or toxic exposure. This is similar as the fibrosis in other organ with inflammation a hallmark of the process. TGFβ1 acts as the most potent profibrotic cytokine by inducing EMT in kidney parenchyma, and promoting fibroblast proliferation and collagen deposition. Among the three target organs of above kidney should be the one of choice if TGFβ1/COX2 were applied for therapy deterring fibrogenesis in the organ (FIG. 25).

Example 25

Combinations of TGFβ1/Cox-2 Inhibitors for Tissue Fibrosis

The previous study with a combination of siRNA inhibitors targeting both TGFβ1 and Cox-2 provided interesting results indicating that this type of combination will have greater therapeutic benefit for treatment of scar related conditions. We believe that the combination of inhibitors targeting both TGFβ1 (or its receptor) and Cox-2 will be much more effective for scar treatment. The small molecule compounds targeting either TGFβ1 or its receptor: SB-431542, Gleevec, AG1296 can be combined with Cox-2 inhibitors such as Vioxx (rofecoxib), Celebrex (celecoxib), and Bextra (valdecoxib) for scar-related conditions. The monoclonal antibody targeting TGFβ1 could also be applied along with the Cox-2 inhibitors.

SB-431542 is a novel, small molecule ATP-mimetic inhibitor of the kinase activity associated with members of the activin receptor-like kinase (ALK) family—specifically ALK5 (TGFβ type I receptor, TGF-βRI), ALK4 (activin type I receptor), and ALK7. SB-431542 can inhibit TGFβ1-mediated activation of SMAD2 and induction of fibronectin and collagen expression in TGFβ1-response cell lines. A recent report showed that SB-431542 blocked TGF-β-mediated increase in proliferation in a mesenchymal cell line. Some investigators described an analysis of the potential therapeutic benefit in a cancer that is dependent on TGF-β. Treatment of glioma cultures with SB-431542 blocks activation of the TGF-β pathway and expression of important effectors of the TGFβ-mediated phenotype. SB-431542 inhibits cell proliferation and blocks cell motility, strongly suggesting that small molecule inhibitors of TGF-RI activity may offer novel therapies in the treatment of malignant glioma. Some research groups showed that at a concentration of 1 μM, SB431542 stimulates proliferation, differentiation, and sheet formation of endothelial cells derived from embryonic stem cells, etc. Celecoxib is an NSAID, a selective inhibitor of cyclo-oxygenase-2 (COX-2). Celecoxib is used in the treatment of rheumatoid arthritis and osteoarthritis.

Celecoxib is used to relieve the pain, tenderness, inflammation (swelling), and stiffness caused by arthritis and to treat painful menstrual periods and pain from other causes. It is also used to reduce the number of polyps in the colon and rectum in patients with a disease called familial adenomatous polposis. Celecoxib is in a class of nonsteroidal anti-inflammatory medications (NSAIDs) called COX-2 inhibitors. It works by stopping the body's production of a substance that causes pain and inflammation. COX-2 inhibitors may cause less stomach bleeding and ulcers than similar medications.

Based on our discovery that combinational use of TGFβ1 and Cox-2 inhibitors is able to improve scarless skin wound healing with multiple animal models, we propose that a different drug modality will also have the similar functionalities which can be used for treatment of tissue fibrosis of various organs. We have prepared 5 formulations using DMSO solution with different ratios of the small molecule inhibitors: SB-431542 and Celecoxib. The solution is with 1 mg/ml concentration of the inhibitor or inhibitors. Formulation 1 with 1 mg of SB-431542 in 1 ml DMSO: Formulation 2 with 0.8 mg of SB-431542+0.2 mg of Celecoxib in 1 ml DMSO; Formulation 3 with 0.5 mg of SB-431542+0.5 mg of Celecoxib in 1 ml DMSO; Formulation 4 with 0.2 mg of SB-421542+0.8 mg of Celecoxib in ml DMSO and Formulation 5 with 1 mg of Celecoxib in 1 ml DMSO. The initial tests are going to be using mouse lung fibrosis model followed by several other mouse models for liver and kidney fibrosis.

Example 26

Combinations of TGFβ1/Cox-2 Inhibitors for Cancer Treatment

Based on our understanding of the multiple roles of TGFβ1 protein and Cox-2 enzyme in various types of cancers, we would like to suggest that the combination of the TGFβ1/Cox-2 Inhibitors, either in the form of siRNA or small molecules, or monoclonal antibody, or peptide inhibitor, antisense and other inhibitors will be very effective to treat several types of cancers, such as colon cancer, breast cancer, lung cancer and brain cancer.

REFERENCES

1. Singer A J, Clark R A: Cutaneous wound healing. *N Engl J Med* 1999, 341:738-746.
2. Martin P: Wound healing: aiming for perfect skin regeneration. *Science* 1997, 276:75-81.
3. Rowlatt U: Intrauterine wound healing in a 20 week human fetus. *Virchows Arch A Pathol Anat Histol* 1979, 381:353-361.
4. Lin R Y, et al. Exogenous transforming growth factor-beta amplifies its own expression and induces scar formation in a model of human fetal skin repair. *Ann Surg* 1995, 222:146-154.
5. Cowin A J, et al. Expression of TGFβ and its receptors in murine fetal and adult dermal wounds. *Eur J Dermatol* 2001, 11:424-431.
6. Krummel T M, et al. Transforming growth factor beta (TGFβ) induces fibrosis in a fetal wound model. *J Pediatr Surg* 1988, 23:647-652.
7. Lanning D A, et al. TGFβ1 alters the healing of cutaneous fetal excisional wounds. *J Pediatr Surg* 1999, 34:695-700.
8. Soo C, et al. Ontogenetic transition in fetal wound transforming growth factor-beta regulation correlates with collagen organization. *Am J Pathol* 2003, 163:2459-2476.
9. Sullivan K M, et al. A model of scarless human fetal wound repair is deficient in transforming growth factor beta. *J Pediatr Surg* 1995, 30:198-202202-193.
10. Stelnicki E J, et al. A new in vivo model for the study of fetal wound healing. *Ann Plast Surg* 1997, 39:374-380.
11. Whitby D J and Ferguson M W: Immunohistochemical localization of growth factors in fetal wound healing. *Dev Biol* 1991, 147:207-215.
12. Roberts A B, et al. Transforming growth factor type beta: rapid induction of fibrosis and angiogenesis in vivo and stimulation of collagen formation in vitro. *Proc Natl Acad Sci USA* 1986, 83:4167-4171.
13. Shah M, et al. Neutralising antibody to TGFβ 1, 2 reduces cutaneous scarring in adult rodents. *J Cell Sci* 1994, 107:1137-1157.
14. Shah M, et al. Control of scarring in adult wounds by neutralising antibody to transforming growth factor beta. *Lancet* 1992, 339:213-214.
15. Choi B M, et al. Control of scarring in adult wounds using antisense transforming growth factor-beta 1 oligodeoxynucleotides. *Immunol Cell Biol* 1996, 74:144-150.
16. Wu K K: Cyclooxygenase 2 induction: molecular mechanism and pathophysiologic roles. *J Lab Clin Med* 1996, 128:242-245.
20. Wilgus T A, et al. Topical application of a selective cyclooxygenase inhibitor suppresses UVB mediated cutaneous inflammation. *Prostaglandins Other Lipid Mediat* 2000, 62:367-384.
21. Sun W H, et al. Cyclooxygenase-2 inhibitors suppress epithelial cell kinetics and delay gastric wound healing in rats. *J Gastroenterol Hepatol* 2000, 15:752-761.
22. Guo J S, et al. Antiangiogenic effect of a highly selective cyclooxygenase-2 inhibitor on gastric ulcer healing in rats. *Toxicol Appl Pharmacol* 2002, 183:41-45.
23. Simon A M, et al. Cyclooxygenase 2 function is essential for bone fracture healing. *J Bone Miner Res* 2002, 17:963-976.
24. Blomme E A, et al. Selective cyclooxygenase-2 inhibition does not affect the healing of cutaneous full-thickness incisional wounds in SKH-1 mice. *Br J Dermatol* 2003, 148:211-223.
25. Muller-Decker K, et al. The effects of cyclooxygenase isozyme inhibition on incisional wound healing in mouse skin. *J Invest Dermatol* 2002, 119:1189-1195.
26. Muscara M N, et al. Wound collagen deposition in rats: effects of an NO-NSAID and a selective COX-2 inhibitor. *Br J Pharmacol* 2000, 129:681-686.
27. Futagami A, et al. Wound healing involves induction of cyclooxygenase-2 expression in rat skin. *Lab Invest* 2002, 82:1503-1513.
28. Wilgus T A, et al. Reduction of scar formation in full-thickness wounds with topical celecoxib treatment. *Wound Repair Regen* 2003, 11:25-34.
29. Mack, J. A. et al. HoxB13 knockout adult skin exhibits high levels of hyaluronan and enhanced wound healing. *FASEB J.* 2003 July; 17(10):1352-4. Epub 2003 May 20.
30. Mack, J. A. et al. HoxB13 up-regulates transglutaminase activity and drives terminal differentiation in an epidermal organotypic model. *J Biol Chem.* 2005 Aug. 19; 280(33): 29904-11. Epub 2005 Jun. 17.
31. Stelnicki, E. J. et al. Modulation of the human homeobox genes PRX-2 and HOXB13 in scarless fetal wounds. *J Invest Dermatol.* 1998 July; 111(1):57-63.
32. Wilgus, T. A. et al. Reduction of scar formation in full-thickness wounds with topical celecoxib treatment. *Wound Repair Regen.* 2003 January-February; 11(1):25-34.
33. Manus, M. T. and P. A. Sharp (2002) Gene silencing in mammals by small interfering RNAs. *Nature Review, Genetics.* 3(10):737-747.
34. Lu, P. Y. et al. (2003) siRNA-mediated antitumorigenesis for drug target validation and therapeutics. *Current Opinion in Molecular Therapeutics.* 5(3):225-234.
35. Kim, B. et al. (2004) Inhibition of ocular angiogenesis by siRNA targeting vascular endothelial growth factor-pathway genes; therapeutic strategy for herpetic stromal keratitis. *Am. J. Pathol.* 165 (6): 2177-85.
36. Tuschl, Zamore, Lehmann, Bartel and Sharp (1999), *Genes & Dev.* 13: 3191-3197.
37. Elbashir, Lendeckel and Tuschl (2001). *Genes & Dev.* 15: 188-200.

38. Kim, D H, J. J. Rossi et al. Synthetic dsRNA Dicer substrates enhance RNAi potency and efficacy. *Nat Biotechnol.* 2005 February; 23(2):222-6.
39. Reynolds A, et al. Induction of the interferon response by siRNA is cell type- and duplex length-dependent. *RNA.* 2006, 12(6):988-93.
40. Fedorov Y, et al. Off-target effects by siRNA can induce toxic phenotype. *RNA.* 2006, 12(7):1188-96.
41. Lu, P. Y. and M. Woodle (2005) Delivering siRNA in vivo For functional genomics can novel therapeutics. In *RNA Interference Technology.* Cambridge University Press. P 303-317.
42. Lu, P. Y. et al. (2005) Modulation of angiogenesis with siRNA inhibitors for novel therapeutics. *TRENDS in Molecular Medicine.* 11(3), 104-13.
43. Lu P Y, Xie F, Woodle M C. (2005) In vivo application of RNA interference: from functional genomics to therapeutics. *Adv Genet.* 54:117-42.
44. Leng, Q. J. and Mixson A. J. Small interfering RNA targeting Raf-1 inhibits tumor growth in vitro and in vivo. *Cancer Gene Therapy.* (2005), 1-9. See also [http://www.pubmedcentral.nih.gov/articlerender.fcgi?artid=29747; Nucleic Acids Res. 2001 March 15; 29(6): 1334-1340. Copyright © 2001 Oxford University Press Branched co-polymers of histidine and lysine are efficient carriers of plasmids, Qing-Rong Chen, Lei Zhang, Sanford A. Stass, and A. James Mixson]
45. Sutton D. et al. Efficient suppression of secretory clusterin levels by polymer-siRNA nanocomplexes enhances ionizing radiation lethality in human MCF-7 breast cancer cells in vitro. International Journal of Nanomedicine 2006:1(2) 155-162
46. Braun C., et al. Structure/Function Relationships of Polyamidoamine/DNA Dendrimers as Gene Delivery Vehicles, J. of Pharm. Sci., 94(2) (2005).
47. Woodle, M C and P Y Lu, Nanoparticles for RNAi Therapy. *Nanotoday*, August 2005, 34-41.
48. Xie, Y. F., M. Woodle and P Y Lu. Harnessing in vivo siRNA delivery for functional genomics and novel therapeutics. *Drug Discovery Today,* 2006 January; 11(1-2): 67-73.
49. Li B. J. et al, Using siRNA in prophylactic and therapeutic regimens against SARS coronavirus in Rhesus macaque. 2005, *Nature Medicine,* 11, 944-951.

All publications, including issued patents and published patent applications, and all database entries identified by url addresses or accession numbers are incorporated herein by reference in their entireties.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition consisting of the siRNA molecule hmTF-25-2 (SEQ ID NO: 36 and SEQ ID NO: 37), the siRNA molecule hmCX-25-1 (SEQ ID NO: 50 and SEQ ID NO: 51), and a pharmaceutically acceptable histidine-lysine polymer, wherein the siRNA molecules and the histidine-lysine polymer form nanoparticles.

2. The composition of claim 1, wherein the nanoparticles have an average size of 150-200 nm.

3. A composition comprising siRNA molecules and a pharmaceutically acceptable carrier, wherein the only siRNA molecules present are the siRNA molecule hmTF-25-2 (SEQ ID NO: 36 and SEQ ID NO: 37) and the siRNA molecule hmCX-25-1 (SEQ ID NO: 50 and SEQ ID NO: 51).

4. The composition of claim 3, wherein the pharmaceutically acceptable carrier comprises a histidine-lysine polymer.

5. The composition of claim 4, wherein the siRNA molecules and the histidine-lysine polymer form nanoparticles.

6. The composition of claim 5 further comprising an additional direct inhibitor to TGFβ1 and/or an additional direct inhibitor to Cox-2, wherein the additional direct inhibitor is selected from the group consisting of small molecule antagonists, monoclonal antibodies, peptide inhibitors, aptamers, and antisense molecules.

7. The composition of claim 5, further comprising a 1, 1.5, 2, 3, or 10 percent concentration of methylcellulose gel.

8. The composition of claim 7, wherein the pharmaceutically acceptable histidine-lysine polymer comprises the histidine-lysine polymer species H3K4b or the histidine-lysine polymer species PT73.

9. the composition of claim 7 wherein the histidine-lysine polymer has the formula (R)K(R)-K(R)-(R)K(X), where R=KHHHKHHHKHHHKHHHK, or R=KHHHKHHHNHHHNHHHN, X=C(O)NH2, K=lysine, H=histidine, and N=asperagine.

10. A composition consisting of the siRNA molecule hmTF-25-2 (SEQ ID NO: 36 and SEQ ID NO: 37), the siRNA molecule hmCX-25-1 (SEQ ID NO: 50 and SEQ ID NO: 51), and a pharmaceutically acceptable carrier.

11. The composition of claim 10, wherein the pharmaceutically acceptable carrier comprises a histidine-lysine polymer.

12. The composition of claim 11, wherein the siRNA molecules and the histidine-lysine polymer form nanoparticles.

13. A method for treating a wound in a mammal, wherein the wound is characterized at least in part by inflammation and neovascularization, comprising administering to the mammal or the wound a therapeutically effective amount of the composition claim 1.

14. The method of claim 13 wherein the treatment results in minimized scar formation.

15. The method of claim 13, wherein the wound is caused by trauma.

16. The method of claim 13, wherein the wound is an ulcer.

17. The method of claim 13, wherein the mammal is a laboratory animal.

18. The method of claim 13, wherein the mammal is a human.

19. The method of claim 13, wherein said administering comprises topical administration to the wound.

20. The method of claim 19, wherein said mammal is a human.

21. A method for treating tissue fibrosis in a mammal caused by scaring after chronic inflammation of the tissue, wherein the tissue is part of the liver, lung, kidney or heart of the mammal, comprising the step of administering a therapeutically effective amount of the composition of claim 1 to the mammal or the tissue.

22. The method of claim 21, wherein the mammal is a laboratory animal.

23. The method of claim 21, wherein the mammal is a human.

24. A method for treating a wound in a mammal comprising administering to the mammal or the wound a therapeutically effective amount of the composition of claim 3.

25. A method for treating tissue fibrosis in a mammal caused by scaring after chronic inflammation of the tissue, wherein the tissue is part of the liver, lung, kidney or heart of the mammal, comprising the step of administering a therapeutically effective amount of the composition of claim 3 to the mammal or the tissue.

26. A method for treating a wound in a human, wherein the wound is characterized at least in part by inflammation and neovascularization, comprising administering to the wound a therapeutically effective amount of the composition claim 7.

27. A method for treating a wound in a human, wherein the wound is characterized at least in part by inflammation and neovascularization, comprising administering to the wound a therapeutically effective amount of the composition claim 8.

28. A method for treating a wound in a mammal, comprising administering to the mammal or the wound a therapeutically effective amount of the composition claim 10.

29. A method for treating tissue fibrosis in a mammal caused by scaring after chronic inflammation of the tissue, wherein the tissue is part of the liver, lung, kidney or heart of the mammal, comprising the step of administering a therapeutically effective amount of the composition of claim 10 to the mammal or the tissue.

30. The method of claim 28, wherein the mammal is a human.

31. The method of claim 29, wherein the mammal is a human.

32. The method of claim 24, wherein the mammal is a human.

33. The method of claim 25, wherein the mammal is a human.

34. A method for treating a wound in a mammal comprising administering to the mammal or the wound a therapeutically effective amount of the composition of claim 6.

35. A method for treating tissue fibrosis in a mammal caused by scaring after chronic inflammation of the tissue, wherein the tissue is part of the liver, lung, kidney or heart of the mammal, comprising the step of administering a therapeutically effective amount of the composition of claim 6 to the mammal or the tissue.

36. The method of claim 34, wherein the mammal is a human.

37. The method of claim 35, wherein the mammal is a human.

* * * * *

SEQUENCE LISTING

```
<160> NUMBER OF SEQ ID NOS: 85

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctactgtgtg ctgagcacct t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgctgctcgg ccactctggc t                                              21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaagccttc tccaacctct                                                20

<210> SEQ ID NO 4
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggatacacct ctccaccaat                                                    20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctccagctcc tgtgccttat                                                    20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgcggcagc tgtacattga cttt                                               24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtgttggtt gtagagggca agga                                               24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actgggccat ggagtggact taaa                                               24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aactgcaggt tctcagggat gtga                                               24

<210> SEQ ID NO 10
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atggccagtt acctggatgt gtct                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaatggacc tggtgggttc tgtt                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggtaccacc atgtacccag gcat                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
actcctgctt gctgatccac atct                                          24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagcctgagg ccgactacta                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggagctctg atgtgttgaa                                               20

<210> SEQ ID NO 16
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 16
attcccttcc ttcgaaatgc                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggggatcagg gatgaacttt                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgtcaccgga gttgtgcggc                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggagctgtg caggtgctgg                                               20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atcagaagcg aggaccagct ttca                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acttgagtgt ctttggctgt cgga                                          24

<210> SEQ ID NO 22
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 22
cacgccatcc tgcgtcgga                                                19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agcaccgtgt ggcgtagag                                                19

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cccaagggcu accaugccaa cuucu                                         25

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agaaguuggc augguagccc uuggg                                         25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ggucuggugc cuggucugau gaugu                                         25

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
acaucaucag accaggcacc agacc                                         25

<210> SEQ ID NO 28
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 28
gguggcugga acagccagau guguu                                              25

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aacacaucug gcuguccag ccacc                                               25

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gaggagccuu caggauuaca agauu                                              25

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
aaucuuguaa uccugaaggc uccuc                                              25

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gcugacccug aaguucaucu gcauu                                              25

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aaugcagaug aacuucaggg ucagc                                              25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 34
ggauccacga gcccaagggc uacca					25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugguagcccu ugggcucgug gaucc					25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cccaagggcu accaugccaa cuucu					25

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
agaaguuggc augguagccc uuggg					25

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gagcccaagg gcuaccaugc caacu					25

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aguuggcaug guagcccuug ggcuc					25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
gauccacgag cccaagggcu accau                                              25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
augguagccc uugggcucgu ggauc                                              25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cacgagccca agggcuacca ugcca                                              25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
uggcauggua gcccuugggc ucgug                                              25

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaggucaccc gcgugcuaau ggugg                                              25

<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ccaccauuag cacgcgggug accuc                                              25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 46
guacaacagc acccgcgacc gggug                                     25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cacccggucg cgggugcugu uguac                                     25

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
guggauccac gagcccaagg gcuac                                     25

<210> SEQ ID NO 49
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
guagcccuug ggcucgugga uccac                                     25

<210> SEQ ID NO 50
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ggucuggugc cuggucugau gaugu                                     25

<210> SEQ ID NO 51
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
acaucaucag accaggcacc agacc                                     25

<210> SEQ ID NO 52
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
```
gagcaccauu cuccuugaaa ggacu                                              25

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
aguccuuuca aggagaaugg ugcuc                                              25

<210> SEQ ID NO 54
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ccucaauuca gucucucauc ugcaa                                              25

<210> SEQ ID NO 55
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uugcagauga gagacugaau ugagg                                              25

<210> SEQ ID NO 56
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gauguuugca uucuuugccc agcac                                              25

<210> SEQ ID NO 57
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gugcugggca aagaaugcaa acauc                                              25

<210> SEQ ID NO 58
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gucuuugguc uggugccugg ucuga                                          25

<210> SEQ ID NO 59
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
ucagaccagg caccagacca aagac                                          25

<210> SEQ ID NO 60
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
gugccugguc ugaugaugua ugcca                                          25

<210> SEQ ID NO 61
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uggcauacau caucagacca ggcac                                          25

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
caccauucuc cuugaaagga cuuau                                          25

<210> SEQ ID NO 63
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
auaaguccuu ucaaggagaa uggug                                          25

<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
caauucaguc ucucaucugc aauaa                                          25

<210> SEQ ID NO 65
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uuauugcaga ugagagacug aauug                                              25

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
gguggcugga acagccagau guguu                                              25

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aacacaucug gcuguccag ccacc                                               25

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gcuggaacag ccagaugugu ugcca                                              25

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uggcaacaca ucuggcuguu ccagc                                              25

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cgccagauua ccaucugguu ucaga                                              25

<210> SEQ ID NO 71
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ucugaaacca gaugguaauc uggcg                                              25

<210> SEQ ID NO 72
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
ggagcccggc aauuaugcca ccuug                                              25

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
caagguggca uaauugccgg gcucc                                              25

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
caaggauauc gaaggcuugc uggga                                              25

<210> SEQ ID NO 75
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ucccagcaag ccuucgauau ccuug                                              25

<210> SEQ ID NO 76
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ggacaagagg cgcaagaucu cggca                                              25

```
<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
ugccgagauc uugcgccucu ugucc                                          25

<210> SEQ ID NO 78
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gcaagaucuc ggcagccacc agccu                                          25

<210> SEQ ID NO 79
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
aggcuggugg cugccgagau cuugc                                          25

<210> SEQ ID NO 80
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ccaucugguu ucagaaccgc cgggu                                          25

<210> SEQ ID NO 81
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
acccggcggu ucugaaacca gaugg                                          25

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
accatctggt ttcagaaccg                                                20

<210> SEQ ID NO 83
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctcctgagga acagtccagc                                                   20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
actggccata ggctggtatg                                                   20

<210> SEQ ID NO 85
<211> LENGTH: 25
<212> TYPE: DNA
<213> ORGANISM: Sus scrofa

<400> SEQUENCE: 85
cccaagggct accatgccaa tttct                                             25
```